United States Patent
Frettlöh et al.

(10) Patent No.: US 11,396,671 B2
(45) Date of Patent: Jul. 26, 2022

(54) SEQUENTIAL CO-CULTURING METHOD FOR PRODUCING A VITAMIN- AND PROTEIN-RICH FOOD PRODUCT

(71) Applicant: Martin Frettlöh, Siegen (DE)

(72) Inventors: Martin Frettlöh, Siegen (DE); Tanja Haag, Siegen (DE); Holger Zorn, Wettenberg (DE); Martina Zajul, Siegen (DE); Jenny Ahlborn, Gießen (DE)

(73) Assignee: Martin Frettlöh, Siegen (DE)

( * ) Notice: Subject to any disclaimer, the term of this patent is extended or adjusted under 35 U.S.C. 154(b) by 0 days.

(21) Appl. No.: 16/632,039

(22) PCT Filed: Jul. 23, 2018

(86) PCT No.: PCT/EP2018/069920
§ 371 (c)(1),
(2) Date: Jan. 17, 2020

(87) PCT Pub. No.: WO2019/016407
PCT Pub. Date: Jan. 24, 2019

(65) Prior Publication Data
US 2020/0149084 A1 May 14, 2020

(30) Foreign Application Priority Data

Jul. 21, 2017 (DE) ............ 10 2017 212 564.0

(51) Int. Cl.
| | |
|---|---|
| *C12P 39/00* | (2006.01) |
| *C12P 19/42* | (2006.01) |
| *C12N 1/14* | (2006.01) |
| *A23L 31/00* | (2016.01) |
| *A23L 33/16* | (2016.01) |
| *A23L 33/15* | (2016.01) |
| *C12N 1/20* | (2006.01) |
| *C12P 21/00* | (2006.01) |

(52) U.S. Cl.
CPC ............ *C12P 39/00* (2013.01); *A23L 31/00* (2016.08); *A23L 33/15* (2016.08); *A23L 33/16* (2016.08); *C12N 1/14* (2013.01); *C12N 1/20* (2013.01); *C12P 19/42* (2013.01); *C12P 21/00* (2013.01); *A23V 2002/00* (2013.01); *A23Y 2220/71* (2013.01); *A23Y 2320/25* (2013.01)

(58) Field of Classification Search
CPC .......... A23L 33/15; A23L 31/00; A23L 33/16; A23V 2002/00; C12P 19/42; C12P 39/00; C12P 21/00; A23Y 2320/25; A23Y 2220/71; C12N 1/20; C12N 1/14
See application file for complete search history.

(56) References Cited

U.S. PATENT DOCUMENTS 9,938,554 B2 * 4/2018 Svagelj ................ C12P 39/00
2009/0148558 A1 6/2009 Kim et al.

FOREIGN PATENT DOCUMENTS

| CN | 105707863 A | 6/2016 |
|---|---|---|
| CN | 105852100 A | 8/2016 |
| DE | 202010016402 U1 | 2/2011 |
| DE | 102016110653 A1 | 12/2017 |
| EP | 1094719 B1 | 5/2003 |
| EP | 2580316 A2 | 4/2013 |
| WO | 2007/139321 A1 | 12/2007 |
| WO | 2015/169967 A1 | 11/2015 |
| WO | 2016/113744 A1 | 7/2016 |

OTHER PUBLICATIONS

Yousef M. et al., "Capability of Lactobacillus reuteri to Produce an Active Form of Vitamin B12 under Optimized Fermentation Conditions", Journal of Academia and Industrial Research (JAIR), vol. 2, Issue 11 (Apr. 2014), pp. 617-621. (Year: 2014).*
Zhu X., Dissertation entitled "Vitamin B12 production during Tofu fermentation by Lactobacillus reuteri and Propionibacterium freudenreichii", Dissertation, submitted on Jun. 2013, Division of Food Microbiology and Biotechnology, Department of Chemistry, University of Hamburg, Germany, pp. 1-186. (Year: 2013).*
Csapo-Kiss et al., Composition of mares' colostrum and milk. Protein content, amino acid composition and contents of macro and micro-elements. International Dairy Journal. 1995;5(4):403-15.
Hugenschmidt et al., Concurrent high production of natural folate and vitamin B12 using a co-culture process with Lactobacillus plantarum SM39 and Propionibacterium freudenreichii DF13. Process Biochemistry. May 2011;46(5):1063-70.
Stephan et al., Edible mushroom mycelia of Pleurotus sapidus as novel protein sources in a vegan boiled sausage analog system: functionality and sensory tests in comparison to commercial proteins and meat sausages. European Food Research and Technology. May 2018;244(5):913-24.
Thi et al., Growth of *Lactobacillus paracasei* ssp. paracasei on tofu whey. Int J Food Microbiol. Dec. 15, 2003;89(1):67-75.
International Search Report for Application No. PCT/EP2018/069920, dated Sep. 7, 2018, 6 pages.
De Lage Wierde, Zusammensetzung Stutenmilch pro 100 ml— Stutenmolkerei de Lage Wierde. Retrieved online at: https://www.kraftderstutenmilch.de/informationen/zusammensetzung-stutenmilch/zusammensetzung-stutenmilch-pro-100-ml/. 3 pages, Jan. 1, 2002.

* cited by examiner

*Primary Examiner* — Satyendra K Singh
(74) *Attorney, Agent, or Firm* — McCarter & English, LLP; Steven G. Davis; Wei Song

(57) ABSTRACT

The present invention relates to a method for producing a vitamin- and protein-rich product, to a food product containing the vitamin- and protein-rich product, and to a nutrient medium appropriate for said method on the basis of agricultural tributaries or food tributaries.

14 Claims, 13 Drawing Sheets

SEQUENTIAL CO-CULTURING METHOD FOR PRODUCING A VITAMIN- AND PROTEIN-RICH FOOD PRODUCT

CROSS-REFERENCE TO RELATED APPLICATIONS

This application is a U.S. national stage filing, under 35 U.S.C. § 371(c), of International Application No. PCT/EP2018/069920, filed on Jul. 23, 2018, which claims priority of German Patent Application No. 10 2017 212 564.0, filed on Jul. 21, 2017. The entire contents of each of the aforementioned applications are incorporated herein by reference.

The present invention relates to a method for producing a vitamin- and protein-rich product, a vitamin- and protein-rich product by the process, and food products containing the vitamin- and protein-rich product.

1. PRIOR ART

In view of the steadily growing world population and resources becoming scarcer at the same time, for example of arable land, there is a need for high-quality food, rich in protein and vitamins, from novel food sources. According to the Global Hunger Index, the proportion of undernourished people in developing countries is already today between 1% and 70%. According to estimates by the Food and Agriculture Organization (FAO), corresponding to the growing global demand for food, agricultural yields would have to be increased by 70% by 2050 to ensure an adequate supply.

Nowadays, mainly animal-based foods are used to sufficiently cover the protein requirement. However, their production has an unfavorable energy balance: For example, to produce 1 kg of pork, 4900 L of water, 4 kg of feed, 9.9 m$^2$ of space, a fattening period of at least half a year followed by 3-4 days of slaughtering with simultaneous $CO_2$ emissions of 8.5 kg are required. A further problem in the production of animal-based products is the widespread use of antibiotics in animal keeping, which can lead to formation of resistances by bacteria and, therefore, to ineffectiveness of antibiotics.

Vegetarian products rich in proteins, which, in their outer appearance, resemble meat products, are often based on soy protein. A major disadvantage in the use of soy is the requirement of large agricultural areas for cultivation. Also, more and more genetically modified soy plants are cultivated. Further, soy-based products, specifically products based on pressed soy, do not have a meat-like taste or texture. Imitating the fiber structure is, therefore, realized by means of wheat gluten, which, however, as allergen may lead to intolerances. Soy-containing products also cannot cover the vitamin requirements of vegetarian or vegan consumers, because specifically neither vitamin D nor vitamin B12 is contained in the soy bean.

Moreover, meat substitute products based on milk protein have been developed, which, however, have a high demand for agricultural animal areas on the on hand, and on the other, can lead to intolerances due to the high milk protein content and lactose content.

Also, fungus-based products, specifically molds (ascomycetes, e.g. *Fusarium venenatum*) have been developed. EP1094719B1 describes a process for preparing proteinaceous substance suitable for use in a foodstuff comprising fermentation of fungal cells of the order Mucorales in an aqueous liquid. The liquid contains an assimilable nitrogen (N) source and an assimilable carbon (C) source. In the process, the RNA content of the fungal cells is reduced to below 4.0% by weight. For binding, egg protein may be used, which, however, may cause allergic reactions in the consumer.

Furthermore, many ascomycetes are considered as spoilage agent partially having pathogenic potential. For example, *Aspergillus flavus* produced a carcinogenic mycotoxin. Also, many fusaria are considered as harmful organisms in agriculture and are moreover able to form very tolerant survival forms, i.e. spores, which may lead to problems in biotechnological process control.

US2009/0148558 relates to a method of producing mushroom mycelia-based meat analog, comprising producing mushroom mycelia, mixing the mushroom mycelia with a protein complement and a binding agent and texturizing the mixture into a protein form by extruding the mixture. Cultivating the mushroom mycelia is performed in liquid medium containing sugar cane extract. Also here, egg protein is used as binder.

Besides the different difficulties described above in the prior art in preparing high-quality meat substitute products rich in proteins without reverting to allergens as binders, known processes for preparing meat substitute products specifically disregard the need for sufficient vitamin supply in vegetarian or vegan diet. This specifically applies to vitamin D as well as vitamin B12, which rarely form part in vegetarian diet.

Vitamin D is contained in higher amounts only in few food products, e.g. cod liver oil or fish. The self-synthesis of vitamin D depends on solar irradiation and is only to a limited extent sufficient for covering the vitamin requirements. Vitamin B12 is mainly found in animal products, which is why a deficiency occurs with vegetarian and vegan diets.

Vitamin D can be produced from precursors, such as ergosterol from fungi, by irradiation with UV light. Further, vitamin B12 can be produced by fermentation of microorganisms. In this regard, DE 20 2010 016 402 U1 describes vitamin D2 optimized fungi as functional food or as additive for functional food. From EP2580316A2 *Lactobacillus reuteri* is known as vitamin B12 producer. Microorganisms like *L. reuteri* are able to synthesize hydroxocobalamin, a natural form of vitamin B12. As hydroxocobalamin, however, is an unstable compound, in industrial use, this form is converted to cyanocobalamin with cyanide. However, the cyanide content thus present can have an adverse effect, especially on sensitive people.

The vitamins produced by fermentation can be purified and taken as supplements, e.g. in form of capsules.

Still, there is demand of vegan or vegetarian food products, specifically meat substitute products, and starting materials, respectively, for preparing such food products, which have a good texture suitable for processing and enriched in such vitamins, which otherwise cannot be sufficiently supplied by vegetarian diet.

2. BRIEF DESCRIPTION OF THE INVENTION

The described problem is solved by the method according to the present invention for preparing a vitamin- and protein-rich product.

The present invention first relates to a method for producing a vitamin- and protein-rich product, comprising the steps:
 a) Cultivating of at least one species of the division of Basidiomycota submerged in a nutrient medium containing at least one carbohydrate-containing agricultural tributary or food tributary to obtain a first cultivation product;

b) Addition of at least one vitamin B12-producing species of the genus *Propionibacterium* and/or of the genus *Lactobacillus* to the first cultivation product; and c) Cultivating the at least one species of the genus *Propionibacterium* and/or of the at least one species of the genus *Lactobacillus* in the first cultivation product to obtain a second cultivation product.

The basis of the method for producing the product is formed by proteins from multi-cellular Basidiomycota, usually consumed as edible mushrooms. Safe consumption of the manufactured product is therefore secured. Further, in the present invention, carbohydrate-rich agricultural tributaries or food tributaries are used as substrates for fungi cultivation, allowing for saving resources and waste recycling. Employed may be agricultural tributaries like vegetable and fruit pomace, and isomaltulose molasses, a by-product of sugar production (trade mark name Palatinose). These waste products from the agricultural industry comprise only hardly hydrolysable carbohydrates, which can be used otherwise only to limited extend. Fungi are able to cleave, via using exogenous cellulases, cellulose-containing carbohydrate fragments and use thereof a carbohydrate source. The used fungi form in addition to proteins also dietary fiber like chitin. These dietary fibers, which thus are present in the prepared product, have positive effects on intestinal flora, specifically due to their anti-oxidant, anti-hypertensive, anti-inflammatory, anti-coagulant, anti-carcinogenic, anti-microbial, hypocholesterolemic and anti-diabetic effects. Further, they cause a prolonged feeling of satiety, because as natural swelling agent they bind water.

The common cultivation of Basidiomycota and bacteria provides for a major advantage over separate fermentation reactions, because only one reactor, i.e. fermenter, is required for the production. Therefore, the fermentation process becomes more robust against contaminations. Also, only one harvesting step is required, in case the second cultivation product shall be processed. The common cultivation also means an immense reduction in costs because only one medium is used for both organisms, an automated process succeeds and, thus, operational hours are saved.

Furthermore, in context of the invention, it has been found that the form of co-cultivation of Basidiomycota and bacteria in step c) is decisive for the growth of the bacteria species. Preferably, no or, respectively, only to a limited extend growth of bacteria on a nutrient medium which had been separated after cultivation in step a) from the Basidiomycota species could be measured. Therefore, the form of co-cultivation is decisive for obtaining a product, which is, on the one hand, rich in proteins, preferably due to the Basidiomycota biomass, and, on the other, enriched in vitamin B12 due to the bacterial vitamin bio-synthesis.

In another preferred embodiment, the method is performed in a cultivation vessel. As explained above, the bacteria can thus be directly added to the Basidiomycota culture and can be cultivated in the same cultivation vessel, e.g. a fermenter or reactor. Preferably, the cultivation vessel can have a volume of at least 2 L, preferably of at least 3 L, more preferred at least 4 L.

In a further preferred embodiment, the method is performed without harvesting the at least one species of the division of Basidiomycota from the first cultivation product. This way, the bacteria can be added directly to the cultivation vessel comprising the fungus culture, which, as explained above, facilitates process control and prevents contamination.

In another preferred embodiment, the at least one species of the division of Basidiomycota is selected from the group consisting of *Agrocybe aegerita, Pleurotus roseus, Lentinula edodes, Laetiporus sulphureus, Pleurotus sapidus, Stropharia rugosoannulata* and/or *Wolfiporia cocos*.

These species of Basidiomycota have been shown to be specifically suitable for cultivation and harmless for the future consumer. The mentioned species show high growth rates on agricultural tributaries and food tributaries, respectively, and thus yield high biomass production values.

In another preferred embodiment, the at least one vitamin B12-producing species of the genus *Propionibacterium* is selected from the species *Propionibacterium freudenreichii* sups. *freudenreichii* and/or *Propionibacterium freudenreichii* sups. *shermanii*. In a further preferred embodiment, the at least one vitamin B12-producing species is of the genus *Lactobacillus*, preferably *Lactobacillus reuteri*.

These species of bacteria have been shown to be specifically suitable for cultivation in the nutrient media, in which the Basidiomycota are cultivated first. Also, these species of bacteria have a high vitamin B12 synthesis rate, which is reflected advantageously in the second cultivation product.

In another preferred embodiment, the second cultivation product has a total biomass in the range of 10 to 50 g/L, preferably 15 to 45 g/L, more preferably 20 to 40 g/L based on dry mass.

In another preferred embodiment, the first cultivation product has a total biomass in the range of 5 to 45 g/L, preferably 10 to 40 g/L, more preferably 15 to 35 g/L based on dry mass.

It has turned out that yielding a biomass of the cultivated species of Basidiomycota in this range is advantageous for the subsequent cultivating of the bacteria species. Therefore, under the given nutrient concentrations present after the cultivation of Basidiomycota, the species of bacteria can achieve high division rates and high vitamin B12 synthesis rates. In summary, hereby a product can be prepared, which is rich in proteins, specifically due to the Basidiomycota biomass, and, sufficiently enriched in vitamin B12 due to the bacterial biomass.

In another preferred embodiment, cultivating in step a) is performed at a temperature from 20 to 28° C., preferably 22 to 26° C., most preferably at about 24° C. In another embodiment, cultivating in step a) is performed aerobically. Further, cultivating in step a) can be performed, at a ventilation rate of 0.1 to 0.5 volume air per volume nutrient medium per minute (vvm), preferably 0.2 to 0.4 vvm.

Specifically, cultivating in step a) can be performed at a temperature of 20 to 29° C., preferably 22 to 26° C., most preferably at about 24° C. and aerobically at a ventilation rate of 0.1 to 0.5, preferably 0.2 to 0.4 vvm.

By the selected temperature ranges and/or the selected ventilation rate ranges it can be provided that the species of Basidiomycota have high biomass synthesis rates.

In another embodiment, cultivating in step a) is performed essentially under exclusion of light, preferably under exclusion of day light.

In another embodiment, the at least one carbohydrate-containing agricultural tributary can contain cellulose.

Basidiomycota are able to digest cellulose and, therefore, grow well on cellulose-containing agricultural tributaries.

In another preferred embodiment, the at least one carbohydrate-containing agricultural tributary or food tributary is selected from the group consisting of apple pomace, aronia pomace, spinach pomace, pomegranate pomace, beet molasses, isomaltulose molasses, sunflower seed pomace, onion pomace, draff, grape marc, hay and/or whey.

Specifically, these agricultural tributaries and food tributaries, respectively, have shown high growth rates for the species of Basidiomycota.

In another embodiment, the nutrient medium cannot contain any sugar cane.

By enzymatically digesting cellulose, Basidiomycota do not require disaccharides as present in sugar cane to achieve a sufficient growth rate. This way, the nutrient medium can be designed resource efficient.

Alternatively, the nutrient medium can comprise cellulose. This allows for yielding high growth rates.

Furthermore, the nutrient medium can comprise 5,6-dimethylbenzimidazole. 5,6-Dimethylbenzimidazole is a component of the vitamin B12 complex. By addition to the nutrient medium, a high yield of vitamin B12 in the second cultivation product may be achieved.

Specifically, glucose and/or 5,6-dimethylbenzimidazole can be added together with the at least one vitamin B12-producing species of the genus *Propionibacterium* and/or of the genus *Lactobacillus* to the first cultivation product.

In another preferred embodiment, the nutrient medium used in step a) contains 5 to 25 g/L carbohydrates, preferably 10 to 20 g/L carbohydrates, more preferably 12 to 17 g/L carbohydrates.

In another embodiment, the at least one species of the division of Basidiomycota is pre-cultivated before cultivating in step a), preferably in a liquid nutrient medium, preferably comprising 2% malt extract medium, more preferably under exclusion of light over a period of 1 to 20 days. In a further embodiment, pre-cultivation is performed at a temperature of 20 to 28° C.

In a further preferred embodiment, the nutrient medium used in step a) further contains:
  at least one nitrogen source;
  at least one magnesium source;
  at least one potassium source and/or phosphate source;
  trace elements, wherein the trace elements comprise iron (II), zinc(II), copper(II) and manganese(II) compounds.

The nutrient medium can be adjusted to a pH value of 5-7, preferably 5.5-6.5.

As potassium source and/or phosphate source preferably dipotassium hydrogen phosphate and/or potassium dihydrogen phosphate can be used.

As nitrogen source, ammonium nitrate, L-asparagine and/or yeast extract can be used.

As magnesium source, preferably magnesium sulfate can be used.

Most preferably, the nutrient medium used in step a) contains: 5 to 25 g/L carbohydrates, preferably 10 to 20 g/L carbohydrates, more preferably 12 to 17 g/L carbohydrates, at least one nitrogen source, wherein the at least one nitrogen source is preferably selected from L-asparagine and/or ammonium nitrate and/or yeast extract, most preferably ammonium nitrate or yeast extract, trace elements, comprising iron(II), zinc(II), copper(II) and manganese(II) compounds, a potassium source and/or phosphate source.

This nutrient medium has been shown to be specifically advantageous for cultivating the Basidiomycota in step a) and cultivating the species of bacteria in step c). Both optimal Basidiomycota biomass and optimal vitamin B12 concentrations could be achieved by using such nutrient medium.

In a further embodiment, the nutrient medium may not comprise milk protein.

Thus, the product prepared by the method is suitable for people having a vegan life-style. Additionally, the prepared product is kosher and halal.

Alternatively, the nutrient medium may comprise whey. Whey as food tributary is specifically suitable for increasing the total biomass and the vitamin B12 content in the second cultivation product.

In a further preferred embodiment, in step b) the at least one vitamin B12-producing species of the genus *Propionibacterium* and/or of the genus *Lactobacillus* is added such that a that a total viable count of all added bacteria species is in the range of $10^4$ to $10^{10}$ CFU/ml, preferably $10^5$ to $10^9$ CFU/ml, in the first cultivation product.

In a further preferred embodiment, cultivating the at least one vitamin B12-producing species of the genus *Propionibacterium* and/or of the the genus *Lactobacillus* in step c) is performed until reaching a vitamin B12-concentration in the range of 1 to 20 ng/mL culture, preferably 2 to 15 ng/mL culture, most preferably 3 to 10 ng/mL culture.

In a further embodiment, cultivating the at least one vitamin B12-producing species of the genus *Propionibacterium* and/or of the the genus *Lactobacillus* in step c) is performed at a temperature of 25 to 40° C., preferably 28 to 37° C.

In a further embodiment, cultivating the at least one vitamin B12-producing species of the genus *Propionibacterium* and/or of the genus *Lactobacillus* in step c) is performed at a ventilation rate of less than 0.2 vvm, preferably less than 0.1 vvm, more preferably less than 0.05 vvm.

In a further embodiment, cultivating the at least one vitamin B12-producing species of the genus *Propionibacterium* and/or of the the genus *Lactobacillus* in step c) is performed essentially anaerobically.

The vitamin B12-producing bacteria may be aerotolerant or anaerobe. In another embodiment, the vitamin B12-producing bacteria are not aerobe and/or microaerophile. Vitamin B12 biosynthesis thus proceeds preferably via the anaerobic synthesis pathway. In summary, the anaerobic synthesis pathway facilitates process control, because this way, no oxygen ventilation in the culture is required in step c).

In particular, cultivating the at least one vitamin B12-producing species of the genus *Propionibacterium* and/or of the the genus *Lactobacillus* in step c) may be performed at a temperature of 25 to 40° C., preferably 28 to 37° C., essentially anaerobically at a ventilation rate of less than 0.2 vvm, preferably less than 0.1 vvm, more preferably less than 0.05 vvm, most preferably anaerobically.

In another preferred embodiment, the second cultivation product is the vitamin- and protein-rich product.

Thus, the culture may be used directly without further processing steps.

In an alternative, preferred embodiment, the method further comprises the steps of:
  d) Harvesting the at least one species of the division of Basidiomycota and the at least one vitamin B12-producing species of the genus *Propionibacterium* and/or *Lactobacillus* from the second cultivation product;
  e) Drying the harvested at least one species of the division of Basidiomycota and the at least one vitamin B12-producing species of the genus *Propionibacterium* and/or *Lactobacillus* to obtain the vitamin- and protein-rich product.

In another embodiment, harvesting in step d) is performed by filtering the second cultivation product. Filtering may be performed via a filter having a pore size in the range of 7 to 12 μm.

For example, a Büchner funnel may be used for filtering.

In an alternative embodiment, harvesting in step d) is performed by centrifuging the second cultivation product. Centrifuging may be preferably performed at a centrifugal acceleration in the range of 2000 g to 5000 g over a period of 5 to 15 minutes.

In another embodiment, drying in step a) is performed by lyophilizing and/or milling and/or spray drying, preferably by lyophilizing.

In another embodiment, the water content of the dried at least one species of the division of Basidiomycota and of the at least one vitamin B12-producing species of the genus *Propionibacterium* and/or *Lactobacillus*, after step e), is at 1 to 60 percent by weight, preferably at 5 to 30 percent by weight.

In another preferred embodiment, the method of the invention further comprises the step of:

Irradiating the at least one species of the division of Basidiomycota at least partially with a UV-light source, preferably having a wavelength in the range of 250 to 350 nm, wherein the step of irradiating may be performed during the whole process.

Irradiating may be performed in steps a) and/or c). In a further preferred embodiment, irradiating is performed after drying in step e), preferably after lyophilizing.

Irradiation after drying was shown to be particularly efficient. Also, not the whole dried biomass needs to be irradiated, but irradiation of only a portion thereof may be sufficient to achieve the desired vitamin D2 concentration in the total biomass.

In another embodiment, irradiating the at least one species of the division of Basidiomycota at least partially with a UV-light source is performed such that a content of vitamin D2 in the range of 0.1 to 0.5 μg vitamin D2/g dry mass of the at least one species of the division of Basidiomycota is obtained.

This way, the consumption of about 10 to 50 g of the irradiated, dried vitamin- and protein-rich product would be sufficient to cover the daily vitamin D-requirements of 5 μm.

In another preferred embodiment, in step b) further at least one glutaminase-active bacteria species selected from the genus *Lactobacillus* is added, wherein preferably *Lactobacillus rhamnosus* and/or *Lactobacillus reuteri* is added. Preferably the glutaminase-active bacteria species may also be the vitamin B12-producing bacteria species.

Glutaminase-active bacteria are able to convert the amino acid glutamine, which is synthesized by the Basidiomycota, into glutamate. This way, a pleasant taste may be attributed to the prepared product, which may be used as food product, preferably as meat substitute product, already during the process.

By using a single bacteria species, which produces vitamin B12 and is glutaminase-active at the same time, the method may be designed particularly efficient. The second cultivation product thus is enriched in vitamin B12 and does not require any further processing steps for enhancement as regards taste.

In another embodiment, after step e), at least one glutaminase-active bacteria species selected from the genus *Lactobacillus* is cultivated on the product rich in proteins and vitamins, wherein, preferably, *Lactobacillus rhamnosus* and/or *Lactobacillus reuteri* are cultivated.

In another embodiment, after step e), the vitamin- and protein-rich product is subjected to heat treatment, preferably at 40 to 70° C. for a period of 10 to 60 minutes to obtain an RNA-depleted vitamin- and protein-rich product.

This way, by heat treatment, the total RNA content of the product may be reduced and, thus, a health benefit may be achieved.

Preferably, this way a purine-depleted product may be provided which may be consumed in context of a low-purine diet.

The present invention further relates to a vitamin- and protein-rich product obtainable by a method according to any one of the preceding embodiments.

In another embodiment, the vitamin- and protein-rich product may not contain any egg protein.

Egg proteins are frequently used as binders, however, are not required for processing to food products due to the advantageous texture of the Basidiomycota protein portion. This way, the product is suitable for people having egg intolerance.

In a further embodiment, the biologic value of the vitamin- and protein-rich product is at least 50, preferably at least 60, most preferably at least 70.

The present invention further relates to a food product, preferably a meat substitute product or animal feed containing the vitamin- and protein-rich product.

In a further embodiment the food product, containing the vitamin- and protein-rich product, may be selected from meat products, for example spread sausage, salami, ham, schnitzel, gyros, kebab, minced meat, chicken nuggets, skewers, and/or bacon.

It has been shown inter alia, that the vitamin- and protein-rich product has a high stickiness. This way, the vitamin- and protein-rich product preferably is used advantageously in food products made from different types of meat, e.g. kebab, to enhance consistency and texture.

In another embodiment, the food product may not contain any animal proteins.

Preferably, the food product may be a meatless product in form of spread sausage, salami, ham, schnitzel, gyros, kebab, minced meat, chicken nuggets, skewers, and/or bacon.

In a preferred embodiment, the food product may be vegan bratwurst, vegan topping, vegan sausage, vegan nuggets, vegan meatballs, and/or vegan schnitzel.

The food product may contain the vitamin- and protein-rich product in a concentration of 0.1 to 99.9 wt.-%, preferably 0.3 to 80 wt.-% based on the total weight of the food product.

In another embodiment, the food product may contain further plant proteins, in a concentration of at most 80 wt.-%, preferably of at most 65 wt.-% based on the total weight of the food product.

Further, the food product may be a cereal-containing product and/or a potatoe product. Preferably, the vitamin- and protein-rich product may be used as a substitute for gluten in cereal-containing products.

Preferably, the vitamin- and protein-rich product may be used as protein source in these food products. Furthermore, the vitamin- and protein-rich product may enhance taste and texture of food products and substitute gluten.

The present invention further relates to use of the vitamin- and protein-rich product for manufacturing food products, preferably meat substitute products and/or animal feed.

The present invention further relates to a nutrient medium containing:

at least one carbohydrate-containing agricultural tributary or food by-product stream, preferably wherein the at least one carbohydrate-containing agricultural tributary or food tributary is selected from the group consisting of apple pomace, aronia pomace, spinach pomace, pomegranate pomace, beet molasses, isomaltulose molasses, sunflower seed pomace, onion pomace, draff, grape marc, hay and/or whey;

at least one nitrogen source;

at least one magnesium source;

at least one potassium source and/or phosphate source;

trace elements, wherein the trace elements comprise iron (II), zinc(II), copper(II) and manganese(II) compounds.

This nutrient medium has been shown to be particularly suitable for sequential co-cultivation. Specifically, high biomass values, based on the Basidiomycota, and high vitamin B12-values, based on the biosynthesis in the used bacteria, could be achieved.

The nutrient medium may be adjusted to a pH value of 5-7, preferably of 5.5-6.5. As nitrogen source preferably L-asparagine, ammonium nitrate and/or yeast extract may be used. As potassium source and/or phosphate source, preferably dipotassium w hydrogen phosphate and/or potassium dihydrogen phosphate can be used. As magnesium source, preferably magnesium sulfate can be used. The nutrient medium may further comprise glucose and/or 5,6-dimethylbenzimidazole.

The term "agricultural by-product stream" refers to the tributary resulting from the processing of agricultural resources to industrial main products. The term "food by-product stream" refers to the tributary resulting industrial food industry.

The term "vitamin D" is used for the vitamin D group of secosteroids and inter alia comprises previtamin D3, vitamin D2 (ergocalciferol), vitamin D3 (cholecalciferol), unless further specified.

The term "vitamin B12" is used for the group of cobalamins and comprises inter alia aqua cobalamin, hydroxocobalamin, methyl cobalamin, cyanocobalamin, adenosyl cobalamin.

The term "cultivating" refers to the growth and/or the reproduction of organisms, and, therefore, the increase in their biomass. The term "fermentation" is presently used synonymously to "cultivating".

3. SHORT DESCRIPTION OF THE FIGURES

4. DETAILED DESCRIPTION OF THE INVENTION

Figure 1:
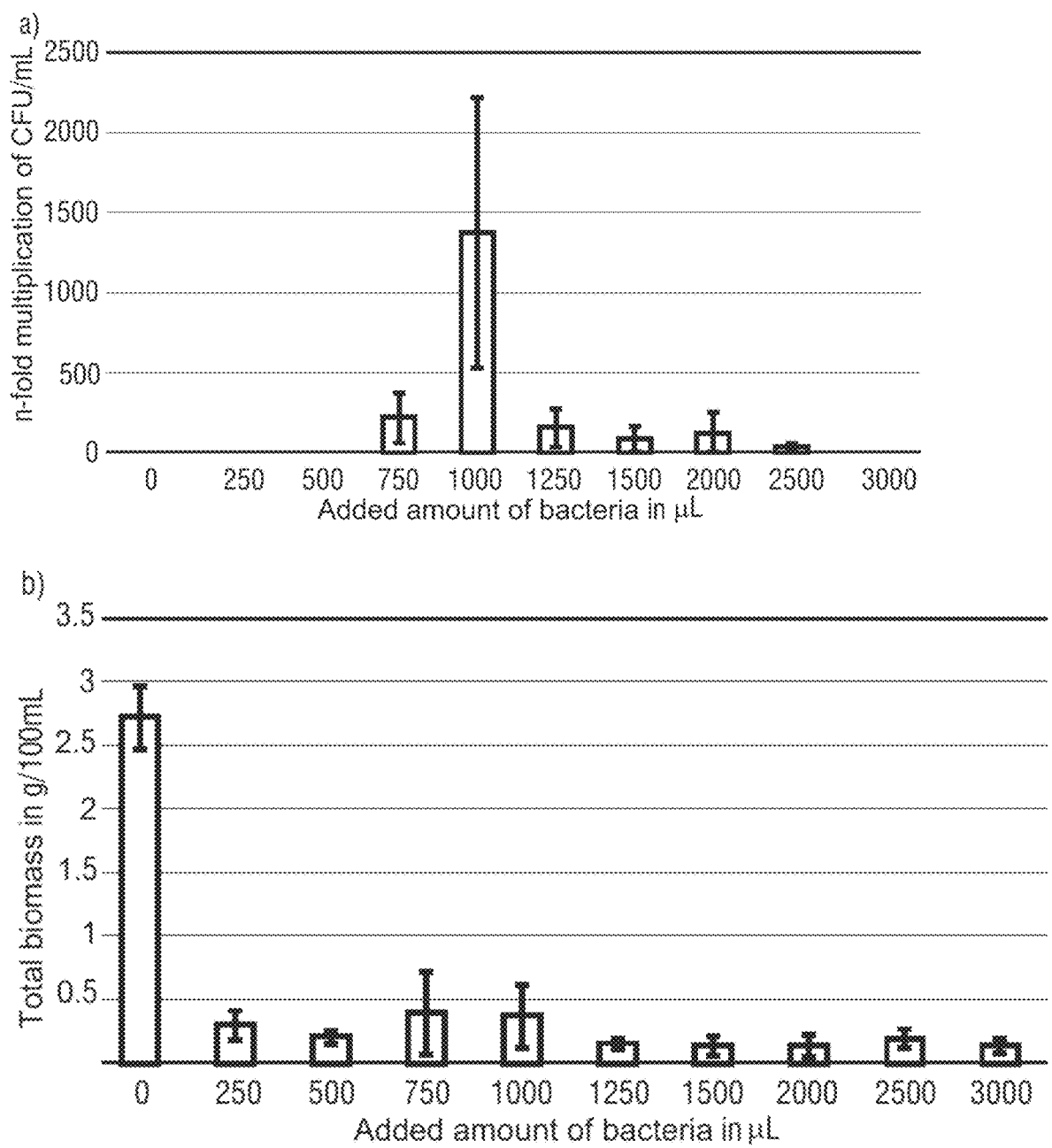
FIG. 1a shows the growth of bacteria of a bacteria culture consisting of *P. freudenreichii* subspecies *shermanii* and *P. freudenreichii* subspecies *freudenreichii* as n-fold increase of the initial added amount in CFU/mL.
FIG. 1b shows the growth of bacteria of a bacteria culture consisting of *P. freudenreichii* subspecies *shermanii* and *P. freudenreichii* subspecies *freudenreichii* as the total biomass including *Pleurotus sapidus* (PSA) in g/100 ml determined by weighing the harvested and dried biomass.

The present invention is based on the submerged co-cultivation of Basidiomycota species and vitamin B12-producing bacteria species in a nutrient medium. The nutrient medium preferably comprises agricultural tributaries or food tributaries, which comprise monosaccharides, disaccharides and/or oligosaccharides and/or which may be cellulose or starch-containing. Preferably, isomaltulose molasses from the production of isomaltulose, carotte pomace, apple pomace pomegranate pomace, spinach pomace and/or beet molasses are used as agricultural tributaries. Food tributaries may comprise draff, grape marc and/or whey. Preferably, cultivation of the Basidiomycota is performed aerobically at a temperature of between 20 and 28° C., until sufficient biomass is provided. Subsequently, in the nutrient medium, cultivation of vitamin B12-producing bacteria is performed, preferably of the genus *Lactobacillus* and/or *Propionibacterium*. The employed bacterial strains preferably are microorganisms which may already be safely used in food production and are considered as GRAS organisms ("generally recognized as safe"). For the cultivation of bacteria species, the temperature is raised to a temperature favorable for bacteria growth. Furthermore, anaerobe conditions may be realized.

During cultivation of the Basidiomycota species, the cultivation of the bacteria species in the nutrient medium, during harvesting, and/or during lyophilization of the harvested species, vitamin D2 may be produced in the Basidiomycota by means of UV-B irradiation.

Vitamin D is formed by the human body when exposed to sunlight or taken up with food. Thereby, vitamin D occurs in different forms, of which specifically vitamin D2 (ergocalciferol), occurring in fungi, and vitamin D3 (cholecalciferol), which is contained only in animal food products, are particularly relevant. Both compounds are converted in the liver to the pro-hormone 25-hydroxy cholecalciferol or 25-hydroxy ergocholecalciferol and subsequently converted to the vitamin D hormone 1α,25-dihydroxy cholecalciferol or 1α,25-dihydroxy ergocholecalciferol, respectively, in the kidney. Chanterelles contain, for example, 2.1 µg/100 g, mushrooms 1.9 µg/100 g vitamin D2. In addition, fungi have a high proportion of ergosterol, which is converted into vitamin D2 by irradiation with UV-B light sources. Thus, during the method of the invention, by irradiation causing a conversion of ergosterol to vitamin D2, a significant benefit may be achieved in the prepared product.

The production of vitamin D2 may preferably performed via irradiation both in the submerged culture and the lyophilized variant of the mycelium. Hereby, the point in time of the irradiation may be chosen flexibly.

Subsequent to cultivation of fungi and bacteria, the harvest of the obtained fermentation products takes place. These are subsequently processed to powders by drying technologies like lyophilization, milling or spray drying. The water content in the prepared product typically is in the range of 1 to 15 percent by weight. The fermentation product may, however, also be processed at high water content.

Depending on the agricultural tributary or food tributary used, the powder appears light or brownish. Depending on the later application, different combinations of fungi and agricultural tributary/food tributary may be used. The protein powder has a neutral, nutty or fungus-like taste depending on the starting substrate used.

Drying results in a product having a high protein and dietary fiber content, and, low fat content at the same time. When analyzing the technological properties, it turned out, that the water binding capacity, the oil binding capacity or the emulsifiability are comparable to those of plant proteins. Furthermore, the Maillard reaction is comparable to meat products. Additionally, in the fungal protein, the stickiness vis-à-vis plant proteins is increased. Likewise, parameters like hardness, chewability and gumminess are comparable, or, specifically regarding chewability, even better than for plant proteins. As to elasticity and stickiness when heated, there is likewise no difference to plant proteins. In total, the fungal protein has throughout better or almost as good as techno functional properties as plant proteins. In comparison to other food products, the biologic value is surprisingly high (e.g. *Pleurotus sapidus* cultivated on isomaltulose molasses: value of 73). As reference of a value of 100, hereby whole egg was used.

Processing of the product may follow known recipes from sausage preparation.

In context of the present invention, the following processes and measurement procedures are used:

1. Submerged Cultivation of Basidiomycota

The submerged cultivation of Basidiomycota may be performed with different carbohydrate-containing agricultural tributaries or food tributaries, for example molasses from sugar production, cellulose-containing products from juice production such as carotte pomace and/or apple pomace or shells or press cakes from the oil production like sunflower seed shells and/or sunflower seed pomace or all further cellulose-containing agricultural tributaries or food tributaries.

For cultivation, the Basidiomycota may be grown on malt extract agar (for example, 20 g/L malt extract, 15 g/L agar agar). For this, the agar plates are inoculated with an about 1 cm² large piece of agar, vegetated with mycelium, sealed with parafilm, and cultivated in a incubator at 24° C., e.g. for 7 days. The plates vegetated to about 80% are stored at 4° C. and regularly over-inoculated according to the same procedure.

For preparing a preculture, a 2 cm² large malt extract agar piece, vegetated with Basidiomycota is added under sterile conditions to 200 mL of a 2% sterile malt extract medium (1 cm²/100 mL). The culture may be homogenized with a mixer; but this is not absolutely necessary. The incubation, for obtaining growth of Basidiomycota, may, for example, be carried out at 24° C., shaking (150 rpm) under the exclusion of light for 4-19 days (cf. Table 1).

TABLE 1

Preculture periods of different Basidiomycota species in days [d].

| Strain | Preculture periods [d] |
|---|---|
| AAE (*Agrocybe aegerita*) | 11 |
| LED (*Lentinula edodes*) | 13 |
| LSU (*Laetiporus sulphureus*) | 13 |
| PSA (*Pleurotus sapidus*) | 6 |
| PEO (*Pleurotus roseus*) | 6 |
| SRU (*Stropharia rugosoannulata*) | 7 |
| WCO (*Wolfiporia cocos*) | 7 |

For the Basidiomycota main culture, for example minimal medium M1 (4.5 g/L L-asparagine monohydrate; 2.4 g/L ammonium nitrate, 1.5 g/L potassium hydrogen phosphate, 0.5 g/L magnesium sulfate, 1 ml/L trace element solution (0.5 g/L iron (II) sulfate heptahydrate, 0.5 g/L zink sulfate heptahydrate, 0.002 g/L copper(II) sulfate pentahydrate, 0.002 g/L manganese(II) chloride tetrahydrate)) may be combined with a defined amount of substrate (cf. Table 2) in an Erlenmeyer flask (sealed with a stopper) and the obtained medium be adjusted to a pH value of 6 and sterilized in the autoclave for 20 min at 120° C.

TABLE 2

Amounts of weighted agricultural tributary substrates in minimal medium M1 to obtain a uniform carbohydrate content of 15 g/L.

| Agricultural tributary substrate | Concentration [g/L] |
|---|---|
| Fresh apple pomace (AT) | 112 |
| Apple pomace (ATD) | 24.6 |
| Aronia pomace (ARO) | 27.1 |
| Lyophilized spinach | 32.3 |
| Pomegranate pomace | 19.3 |
| Beet molasses | 27.2 |

Subsequently, the Basidiomycota pre-culture is added to the medium mixture having a final concentration of 10% fungus pre-culture. Cultivation is carried out for 7-14 days at 24° C., shaking (150 rpm) under exclusion of light in the incubator. After full vegetation of the cultures, they are centrifuged for 10 min at 3283 g and the mycelium is washed three times with deionized water (DI water). In case of isomaltulose molasses as residue substrate, preferably M2 medium may be used for the cultivation of the Basidiomycota. The composition of the M2 medium is as follows: 3 g/L yeast extract, 1.5 g/L potassium dihydrogen phosphate, 0.5 g/L magnesium sulfate hydrate, 1.0 mL trace element solution. Per 100 ml M2 medium 10 ml Palatinose are added. The further procedure corresponds to the one described above.

2. Cultivation of the Basidiomycota in the 7.5 L Fermenter

The fermenter is loaded with 5 L medium and a corresponding amount of substrate, the pH value is adjusted with 1M caustic soda to 6.0 and autoclaved. Inoculation is performed with 500 mL Basidiomycota pre-culture. The settings of the fermenters are: 150 rpm stirrer speed, 24° C. temperature and 0.3 vvm ventilation rate. The obtained fermentation products are subsequently processed by lyophilization at −70° C., 37 mbar pressure, until a specific water content of 8 to 12 weight-%.

3. Co-Cultivation of the Basidiomycota and Vitamin B12-Producers as Well as Glutaminase-Active Bacteria Illustrated by the Example of *Pleurotus Rapidus* (PSA) with *Propionibacterium freudenreichii* and *Lactobacillus reuteri* Cultivated on the Industrial Tributary Isomaltulose Molasses For co-cultivation of Basidiomycota and bacteria, first a pre-culture of *Pleurotus sapidus* (PSA) is grown. For this, a 2 cm² large piece of malt extract agar vegetated with PSA is added under sterile conditions to 200 mL of a 2% sterile malt extract medium. The culture may be homogenized by means of a mixer (at maximum power level); this, however, is not absolutely necessary. Subsequently, incubation is carried out at 24° C., shaking (150 rpm) under exclusion of light for 7 days.

Subsequent to successful growing the pre-culture, the main culture is inoculated. For this, 90 mL minimal medium M1 or M2 are combined with 10 mL isomaltulose molasses in an Erlenmeyer flask (sealed with a stopper), and the obtained medium is adjusted to a pH value of 6 and sterilized in the autoclave for 20 min at 120° C. Subsequently, the Basidiomycota pre-culture is added to the medium mixture having a final concentration of 10% fungus pre-culture. Cultivation is carried out for 7 days at 24° C., shaking (150 rpm) under exclusion of light in the incubator.

In parallel, pre-cultures of *Lactobacillus reuteri* (*L. reuteri* DSM20016) and *Propionibacterium freudenreichii* (*P. freudenreichii*) subsp. *freudenreichii* (DSM20271) and *shermanii* (DSM4902) are made. For this, 10 μL of a common glycerol stock of the corresponding bacteria are added to 10 mL of the corresponding optimum medium (for *L. reuteri*: B12 assay medium (ready-made medium from Sigma Aldrich, St. Louis USA); for *P. freudenreichii*: Propionibacterium medium (5 g/l Caseinpepton, 10 g/l yeast extract, 16.8 g/L DL sodium lactate; pH value 6.7+/−0.2) and incubated over night at 30° C. (*Propionibacterium*) or 37° C. (*L. reuteri*) under anaerobe conditions (Wheaton tubes). The pre-cultures are adjusted to a bacteria concentration of about $6*10^9$ CFU/mL, to obtain a final concentration in the PSA culture of about $6*10^7/100$ mL. The initial $OD_{595\ nm}$ in the fungus cultures with bacteria should be about 0.3 at the starting point.

To the PSA culture aerobically cultivated for over 7 days, 1 mL of bacteria pre-culture (*L. reuteri* or mixture of *P. freudenreichii* subsp. *shemanii* and subsp. *freudenreichii*) is added and the cultures are incubated under anaerobe conditions in anaerobic pot with gaspack at 30° C. (culture with *P. freudenreichii*) or 37° C. (culture with *L. reuteri*) for 2 days. Subsequently, harvest of the protein pellet is carried out as explained in the following section. As negative control and for comparison of the Basidomycota growth without bacteria, a PSA culture without addition of the bacteria suspension is run along. The temperatures of the incubation period are maintained.

The bacterial growth was determined by application of classical microbiological counting methods (*L. reuteri* on MRS agar; *Propionibacterium* on Propionibacterium agar) and, additionally, by determination of the OD at 595 nm at the point in time 0, i.e. directly after addition of the bacteria to the PSA main culture as well as at the end of the cultivation or before harvest.

The total biomass was determined after harvest by weighing. First, wet weight was determined by weighing, subsequently the proteinpellet was dried at 80° C. and the weight was determined again. For this, the whole culture was put into a Büchner funnel which was equipped with a filter paper having a pore size of 7-12 μm. The Büchner funnel is first mounted on a suction bottle to which a vacuum pump is connected. By means of the vacuum pump, the whole liquid in the mycelium is filtrated by suction. The mycelium on the filter is put into an empty petri dish, of which the tara was defined and dried at 80° C. Subsequent to complete drying, the total biomass was determined in g on a fine balance.

4. Determination of the Vitamin B12 Content

The determination of the vitamin B12 content in the different samples is conducted by means of an ELISA kit (Cloud-Clone Corp.). The micro titer plate contained in the kit is coated with a monoclonal antibody which specifically acts with cyanocobalamin (CNCbl). Biotin-tagged CNCbl functions as competitor to CNCbl from the samples and employed standards. Both compete for the antibodies on the plate. The binding occurs during a one-hour incubation phase, after which unbound conjugates are washed away. After several washing steps, an avidin-linked horse reddish peroxidase (HRP) is added. The avidin is bound by the biotin from the competitor and after a further incubation step the linked HRP forms, in combination with the substrate solution of the kit, a color complex. The color intensity in the wells is determined by means of measuring the optical density (OD) at 450 nm. It relates anti-proportionally to the CNCbl concentration present in the sample.

Naturally occurring forms of cobalamin cannot be detected by means of the kit but must be converted to cyanocobalamin. A quantification of the cobalamin portions is carried out by employment of a standard series between 0 and 10.000 pg/mL cobalamin, which is run along with the experiments. The determined OD of the standard samples is plotted against the logarithm (log) of the standard concentration. A straight-line results, by which formula the logarithm of the sample OD may be calculated. An inversion of the logarithm provides the cobalamin content of the samples in pg/mL.

The sample preparation for conversion of any cobalamin forms into cyanocobalamin is carried out as follows:

The co-cultures are centrifuged for 10 min at 6.000 rpm, the supernatant rejected, the pellet washed with ddH$_2$O one time. Subsequently, a defined amount of ddH$_2$O is added and mixed with glass balls (diameter 0.25-0.55 mm) in a ratio of 1:2. The cell disruption is carried out by means of ultra sound using a sonicator (Sonifier 250 d Branson) for 10 min at 60% amplitude (1 min pulse, 1 min pause). The disrupted cultures are again centrifuged at 6000 rpm for 10 min. Subsequently the conversion into cyanocobalamin is carried out by addition of 10% KCN in a final concentration of 2% KCN in the corresponding culture followed by a 10-minute incubation at room temperature and subsequent storage on ice. Subsequently, ELISA is carried out according to manufacturer's specifications (ELISA KIT for Cyanocobalamin Cloud-Clone Corp.). As control for the conversion of cobalamin to cyanocobalamin, a defined amount of pure hydroxy cobalamin (5.000 pg/mL) is run along.

5. Determination of the Conversion of Glutamin into Glutamate

In the amino acid profile of PSA, high glutamine contents occur, which may be converted into glutamate by using glutaminase-active bacteria. *Lactobacillus rhamnosus* and *Lactobacillus brevis*, for example, may be used as glutaminase-active bacteria. Moreover, it has been shown, that also *Lactobacillus reuteri* has a significant glutaminase activity. In addition to the mere confirmation of the glutaminase activity, it was analyzed subsequently, whether the addition of *L. reuteri* to lyophilized, milled PSA mycelium, cultivated on isomaltulose molasses, leads to conversion of the glutamine contained in the fungus mycelium to glutamate. The procedure for sample preparation as well as for determination of the conversion to glutamate is as follows:

In Wheaton tubes, 0.1 g lyophilized, milled, heat-treated (30 min at 150° C.) PSA mycelium (cultivated with isomaltulose molasses as substrate) is weighted and 300 µl 1M sodium acetate buffer (pH 5.8), 10 µl alcalase 0.1% (v/v) and 800 µl flavourzyme 8% (v/v) are added and completed to 10 ml with H$_2$O. Alcalase and flavourzyme are two enzyme mixtures containing different endo and exo proteases. These are for cleaving the proteins of the fungus mycelium, such that up-take by *L. reuteri* is facilitated. To one of the two batches 5 µL of an *L. reuteri* over-night culture is added, the other one serves a negative control. The incubation of both batches is carried out at 37° C. overnight. Subsequently, the cultures are centrifuged for 10 min at 6.000 rpm, the obtained supernatant rejected, and the pellet is washed with 50 mM sodium phosphate buffer with 1 mM PMSF final concentration and centrifuged for 5 minutes at 6.000 rpm. This procedure is repeated twice. 1 mL of 50 mM sodium phosphate buffer is added to the obtained pellet and the cells are disrupted by means of glass balls in a ratio of 1:2 w/v and vortexer for 10 min. Subsequently it is centrifuged for 10 minutes at 6.000 rpm and the obtained supernatant is transferred in a 1.5 mL reaction vessel. The samples are stored on ice until the analysis by means of a glutamate assay kit (abcam, Cambridge, UK). This measures free glutamate. The contained enzyme mix recognizes glutamate as specific substrate, leading to a proportional color development. This may by measured calorimetrically at an OD of 450 nm. These measurements are carried out with a plate reader Infinite 200 Pro from Tecan.

6. Determination of the Vitamin D Content

By irradiation of the Basidiomycota mycelium with UV-B radiation (Arimed B 12 UV-lamps, JW Sales GmbH, Stuttgart) ergosterol located in the cell membrane may be converted into vitamin D2. Ergosterol and vitamin D2 are identified and quantified by means of HPLC-DAD (Absorption maxima: Ergosterol 282 nm, vitamin D2: 265 nm. The limits of detection and determination are determined according to DIN 32645 (calibration method) with n=7, significance level 99% and k=3. The limit of detection is 1.1 µg/ml, the limit of determination 4.0 µg/ml.

The following system is used.

Columns: Chromolith Performance Reserved/Phase-18 e 100-4.6 mm (length–diameter) (with precolumn) and EC 250/4 Nucleosil 100-5 C18, in series HPLC-DAD: La Chrom System L-7100/L-7200/D-7000/L-7455 from Merck Hitachi Eluents: Methanol, HPLC grade (A), acetonitrile HPLC grade (B) and 0.05% formic acid (C)

| Flow rate: 1 ml/min (gradient) | | | |
|---|---|---|---|
| Gradient: Time (min) | % A | % B | % C |
| 0 | 0 | 70 | 30 |
| 2 | 0 | 100 | 0 |
| 10 | 0 | 100 | 0 |
| 20 | 5 | 95 | 0 |
| 50 | 0 | 100 | 0 |
| 55 | 5 | 95 | 0 |
| 60 | 0 | 70 | 30 |

Injection volume: 10 µl

Software: HPLC System Manager HSM Manager, Version 4.1

Standards: Ergocalciferol (≥98% Sigma), Cholecalciferol (99.9%, Supelco), Ergosterol (≥75.0%, Sigma) and 7-dehydrocholesterol (≥95.0%, Sigma)

The quantification of vitamin D2 was carried out by ratios of peak areas analyte to internal standard of the calibration line and taking into account the sample preparation.

$$\text{Vitamin D2 } [\mu g(gDM)^{-1}] = (\text{vitamin D2 } [\mu g\ ml^{-1}]^* V_{MeOH\ (ml)})/E[g])^*(100/(100-\%\ \text{moisture})$$

$V_{MeOH}$: Volume of methanol, in which the residue was taken-up [ml]

E: sample weight [g]

% moisture: residual moisture determined by means of moisture analyzer

Sample Preparation:

The lyophilized fungus mycelium is milled in liquid nitrogen, about 2 g are weighted into a brown glass round bottom flask and saponificated with 50 mL ethanol, 4 mL sodium ascorbate solution (17.5 g in 100 ml 1M caustic soda), 10 ml KOH/H2=(50/50, w/w) and 0.5 ml internal standard vitamin D3 (200 µg/ml) for 1 h at 80° C. under reflux. Subsequent to addition of 50 ml DI water, cooling to room temperature and filtration, it is extracted with 50 ml diethyl ether, 50 ml n-pentane/10 ml ethanol, 50 ml n-pentane, 20 ml n-pentane. The organic phases were combined, washed trice with 50 mL 3% KOH in 5% ethanol and subsequently washed neutral with DI water, dried over sodium sulfate (overnight, 4° C.), filtered and the solvent reduced to dryness (40° C., rotary evaporator). The residue was taken-up in 1.5 mL methanol, dissolved by ultrasonication for 5 min and centrifuged (10 min, 18.000 g). Subsequent to membrane filtration (0.22 μm), the solution was used for quantification by means of HPLC.

7. Amino Acid Analytics

The identification and quantification of the amino acids in the lyophilized fungus mycelium was carried out by means of amino acid analyzer. For this, the proteins were subjected to a total hydrolysis.

Amino acid analyzer S 433 for protein hydrolysates from Sykam

Columns: Separation column LCA K13 S/N, filter column LCA K04 S/N

Eluents: Sodium citrate buffer solution pH 3.4 (A), Sodium citrate buffer solution, pH 10.85 (B), Regeneration solution (RegSol Na)

Reagent: Ninhydrin, pH 10.85

Washing solution: Ethanol/isopropanol/water (250/250/500 v/v/v)

Flow rate: 0.45 mL min-1 (gradient)

Gradient:

| Time [min] | A [%] | B [%] | RegSol Na [%] |
|---|---|---|---|
| 0 | 100 | 0 | 0 |
| 5 | 100 | 0 | 0 |
| 11 | 95 | 5 | 0 |
| 13 | 80 | 20 | 0 |
| 25 | 70 | 30 | 0 |
| 29 | 30 | 70 | 0 |
| 31 | 20 | 80 | 0 |
| 33 | 10 | 90 | 0 |
| 41 | 0 | 100 | 0 |
| 49 | 0 | 0 | 100 |
| 49.1 | 0 | 0 | 100 |
| 52 | 0 | 0 | 100 |
| 52.1 | 100 | 0 | 0 |

Injection volume: 50 μL

Software: Chromstar, Version 7

Standards: amino acid calibration solution (mixture of amino acids of known concentration for hydrolysates) (Sykam), L-Tryptophan (≥99.0%, Roth).

For quantification of the amino acids a one-point calibration was carried out.

The calculations are performed as follows:

$$m_{(factor)}[\text{mg } DM] = \frac{E - [DM - (DM * \% \text{ moisture}/100])}{V_{(HCl)}} * V$$

$$w_{(AS)}[g\ (100g\ DM)^{-1}] = \frac{c_{(AA)}[\text{mol}] * M_{(AA)}[g\ \text{mol}^{-1}]}{m_{(Factor)}[g]} * 100$$

wherein $m_{(factor)}$ Conversion factor from nmol ml$^{-1}$ to nmol mg$^{-1}$ $DM$ Dry mass with residual moisture in mg % moisture Residual moisture determined by means of moisture analyzer [%]

$E$ Sample weight [mg]

$V_{(HCl)}$ Volume of used 6 M hydrochloric acid (3.4.10.1)

$V_{(Aliquot)}$ Volume of evaporated aliquot $w_{(AA)}$ Mass fraction of each amino acid in g (100g DM)$^{-1}$ $c_{(AA)}$ Molar concentration of an amino acid in mol mL$^{-1}$ $M_{(AA)}$ Molar weight of the corresponding amino acid The sample preparation is carried out as described in the following.

Acid hydrolysis for total amino acid determination:

The lyophilized fungus mycelium is ground in a mortar, about 250 mg are weighted into a pyrex tube and 6 mL 6 M HCl (0.1% phenol) are added. For avoiding oxidation, oxygen is removed by introducing nitrogen. Hydrolysis is carried out for 24 and 48 h at 100° C. in a drying oven. Subsequent to cooling on ice, centrifugation (20 min, 4° C., 3.283 g) and membrane filtered (0.22 μm) are carried out. For separation of the acid, an aliquot (200 μL) is evaporated to dryness at 130° C. and taken-up in 1 mL sample dilution buffer (pH 2.20). Subsequent to diluting with sample dilution buffer (1:5), the solution is used for quantification by means of amino acid analyzer.

Basic hydrolysis for the determination of tryptophan:

The lyophilized fungus mycelium is ground in a mortar, about 250 mg are weighted into a pyrex tube and mixed with 6 mL 5 M NaOH (0.1% phenol). To avoid oxidation, the oxygen is removed by introducing nitrogen. Hydrolysis is carried out for 24 and 48 h at 100° C. in a drying oven. Subsequent to cooling on ice, centrifugation (20 min, 4° C., 3,283 g) and membrane filtration (0.22 μm) are carried out. An aliquot (200 μL) is evaporated to dryness at 130° C. and taken-up into 1 mL sample dilution buffer (pH 2.20). Subsequent to diluting with sample dilution buffer (1:5), the solution is used for quantification by means of amino acid analyzer.

Oxidation before hydrolysis for cystein and methionin determination:

The lyophilized fungus mycelium is ground in a mortar, about 250 mg are weighted into a pyrex tube and 5 mL 5 M oxidation solution (30% H2O2 in 98% formic acid and 0.1% phenol). The pyrex tubes are sealed and incubated for 16 h at 0° C. in an ice bath. By addition of sodium disulfite oxidation was quenched and 5 mL 6 M HCl (0.1% phenol) are added. Hydrolysis is carried out for 24 h at 100° C. in a drying oven. Subsequent to cooling on ice centrifugation is carried out (20 min, 4° C., 3.283 g) and membrane filtered (0.22 μm). The pH value is adjusted to 2.20 by means of 1 M sodium hydroxide. 200 μL are taken for evaporating and the residue is taken-up in 1 mL sample dilution buffer (pH 2.20). Subsequent to diluting with sample dilution buffer (1:5), the solution is used for quantification by means of amino acid analyzer.

8. Biological Value

The biological value (BV) is the best-known method for estimating the quality of proteins in food. It is a measure of how much of an ingested food protein can be converted into proteins of the organism's body.

The biological value results from the following equation:

BV=(retained nitrogen/absorbed nitrogen)*100

The higher the biological value of the absorbed proteins, the less protein needs to be added to achieve a balanced protein and nitrogen balance. The most important criterion for the biological value is the composition of the amino acids in a food. The more proteinogenic amino acids are contained therein and the higher the content of essential amino acids, the higher the protein is classified as being of high value.

Animal proteins generally have a higher biological value than plant proteins. As "reference protein" for the quality assessment of other dietary proteins, whole egg was selected, which is assigned a biological value of 100 or 1.0. The biological value of all other proteins is thus given in comparison to whole egg. However, the reference value "100" of whole egg does not correspond to a 100% conversion of the latter, which means that a value of 100 for the biological value can easily be exceeded, especially by combined foods.

The biological value can be considerably increased by clever food combinations, as the amino acids of different foods complement each other, and deficits can be compensated (supplementary value). The combination of food proteins plays an important role especially in countries where the diet contains only few animal foods.

By means of the following calculation, the biological value is calculated:

$$EAAi: \sqrt[n]{\left(\frac{Ile_T}{Ile_R}*100\right)*\left(\frac{Leu_T}{Leu_R}*100\right)*\left(\frac{Lys_T}{Lys_R}*100\right)}$$

EAAi: Essential Amino Acid Index $BV = 1.09 * EAAi - 11.7$

9. Determination of Mineral Nutrients/Sugars

The samples are digested with aqua regia in a micro wave system. Subsequently an ICP-MS (Inductively coupled plasma mass spectrometry) is carried out. An argon plasma is induced by a high-frequency current and the sample is heated to 5,000-10,000° C. The ions generated in the plasma are accelerated in the direction of the mass spectrometer's analyzer by an electric field, thus enabling the detection of elements and their isotopes.

The determination of glucose and D-fructose and the detection of the conversion of D-glucose and D-fructose from the substrate is carried out enzymatically.

10. Determination of the Total Nitrogen Content According to Kjeldahl (Crude Protein)

The total nitrogen content was quantified according to Kjeldahl (Kjeldahl 1883, modified according to Matissek et al. 2010), each in duplicate determination. The samples were weighted into nitrogen-free vellum boats and digested with a glass ball, half of a catalyst tablet and 15 mL concentrated sulfuric acid in a digestion flask at 400° C. for at least 3 h until the solution had turned into a greenish color. Subsequently a water vapor distillation was carried out. For this, caustic soda and some drops Sher indicator were added to the digestion flask. The formed ammonia was transferred into a boric acid and Sher indicator containing solution. Titration was carried out with 0.1 M hydrochloric standard solution.

The crude protein content was calculated according to the following equation.

$$P\ [\%\ DM] = \frac{a*1.4008*F}{E*10} * \frac{100}{100 - \%\ moisture}$$

P Crude protein content [% DM]

a Consumption of 0.1 M HCl standard solution [mL]

1.40081 mL 0.1 M HCl corresponds to 1.4008 mg nitrogen

-continued

F Conversion factor for calculating the crude protein content (comm. factor for fungi: 4.38, for PSA: 4.97, for LED:4.5)

E Sample weight [g]

10 Conversion factor per 100 g sample and mg nitrogen in g

% moisture Residual moisture determined by means of moisture analyzer [%]

11. Determination of Ash Content

Subsequent to complete incineration at 550° C., the ash content was determined by means of difference weighing of the quartz crucibles. The calculation was carried out according to the following equation:

$$Ash\ [\%\ DM] = \frac{\Delta_{crucible}*100}{E} * \frac{100}{100 - \%\ moisture}$$

$\Delta$crucible Difference of the crucible before and after incineration

Ash Ash content [% DM]

E Sample weight [g]

% moisture Residual moisture determined by means of moisture analyzer [%]

12. Determination of the Total Carbohydrate Content

The total carbohydrate content of the substrates was determined by means of Orcinol-sulfuric acid assay. For this, 10 mg sample were hydrolyzed in 2 mL 2 M HCl (2 h, 100° C., 700 rpm) and, subsequently, membrane filtered. Subsequent to 1:50 dilution with purified water, 800 µL reagent solution (2 g L-1 Orcinol in conc. sulfuric acid) were added to 200 µL hydrolysate (or standard), shaken, and heated for 15 min at 80° C. Subsequent to cooling to room temperature, the total carbohydrate content was determined photometrically at 420 nm against water. Calibration was carried out with glucose (10-100 µg mL-1).

13. Determination of the Proportion of Fungus in the Lyophilizate Via Ergosterol When cultivating fungi on residual streams, substrate components may be present which are not or not completely degraded by the fungus and therefore still exist in the harvested mycelium. The proportion of fungus in this mycelium-substrate mixture can be determined via the ergosterol content, because ergosterol is found exclusively in fungi. To establish a calibration line, the corresponding fungus was cultivated in malt extract medium containing only soluble components and the biomass after cultivation, therefore, consists of 100% fungus mycelium. This was used for the calibration, in which the peak area ratio of ergosterol to 7-DHC (IST) was plotted against the mass of fungus mycelium [g DM].

The sample preparation was carried out as in context of the vitamin D analytics. As internal standard 1 mL 7-dehydrocholesterol (7-DHC, 1 mg mL-1) was used. The absorption maximum of ergosterol and 7-DHC is at 282 nm. Subsequently, quantification was carried out at this wavelength.

14. Treatment of the Mycelium of the Fungus for Reduction of the RNA Proportion

The mycelium of the fungus was subjected to a temperature treatment. For this, temperature ranges of 40-70° C. as well as incubation periods of 0-40 minutes were tested. Before and after the treatment, the crude protein content is determined, and the RNA is subsequently extracted by means of RNeasy® Plant Mini Kit. The quantification of the RNA concentration before and after the heat treatment was carried out by means of capillary gel electrophoresis.

15. Techno Functional Examinations

Water binding capacity/oil binding capacity:

An important parameter for the water-binding ability is the water-binding capacity (WBC). It indicates the mass of water that can be bound by one gram of the product. To determine this parameter, a defined mass of the sample material is saturated with water, whereby the water is added stepwise until the saturation point is reached. Just enough water is added to ensure that only a small aqueous supernatant is formed during centrifugation of the sample material. The advantage of adding an excess of water compared to the stepwise addition is a reduced amount of work. However, the disadvantage is that the excess water also separates soluble components of the sample material. This can lead to a significant falsification of the measurement result. For this reason, it was decided to add the water stepwise.

The oil binding capacity (OBC) is to be considered analogous to the water binding capacity.

WORKED EXAMPLES

The present invention is illustrated below by means of different exemplary processes and product examples which, however, are not to be regarded as limiting.

Example 1

Screening of Different Fungus-Substrate Combinations

As selection criterion the growth [g DM L$^{-1}$], the cultivation duration and the protein yield [g L$^{-1}$], measured according to the method for determining the crude protein content according to Kjeldahl (cf. under 10. "Determination of the total nitrogen content according to Kjeldahl (crude protein)") were used.

Inter alia fresh apple pomace (Fischer) and apple pomace (Döhler) turned out to be highly suitable substrates for the production of Basidiomycota biomass in combination with *Pleurotus sapidus* (PSA) (culture period: 4 days, approx. 14 g DM L$^{-1}$, approx. 3 g L$^{-1}$ protein). Furthermore, also the isomaltulose molasses in combination with PSA (culture period: 4 days, approx. 11 g DM L$^{-1}$, approx. 2.8 g L$^{-1}$ protein), onion pomace in combination with PSA (culture period: 13 days, approx. 34.5 g DM L$^{-1}$, approx. 3 g L$^{-1}$ protein), and carotte pomace in combination with *Lentinula edodes* (LED) (culture period: 6 days, approx. 9 g DM L$^{-1}$, approx. 2.3 g L$^{-1}$ protein) turned out to be promising.

Example 2

Co-Cultivation of *Pleurotus sapidus* and *Propionibacterium freudenreichii*

First, it was tested, which temperature ranges are tolerated by the used organisms. Thereby, it was found out that Basidiomycota show sufficient growth only until 27° C. and do hardly form any biomass after this raise in temperature even at optimum temperature. The used bacteria require higher temperatures for sufficient growth, preferably the optimum temperature for propioni bacteria is at 30° C.

First, *Pleurotus sapidus* (PSA) in minimal medium M1, with 10% (v/v) isomaltulose molasses added, was cultivated for 24 h aerobically (10 ml PSA pre-culture and 90 ml M1/isomaltulose mixture) and, subsequently, different amounts of a bacteria pre-culture having about 6*10$^9$ CFU/ml (*P. freudenreichii* subs. *freudenreichii* and subs. *shermanii*) were added. An incubation for 7 days under switching to anaerobe conditions was carried out at 30° C. Bacteria growth was observed at the end of the incubation period, specifically when using a 1 ml bacteria pre-culture. However, only little PSA growth/total biomass was observed (cf. FIG. 1).

Figure 2:
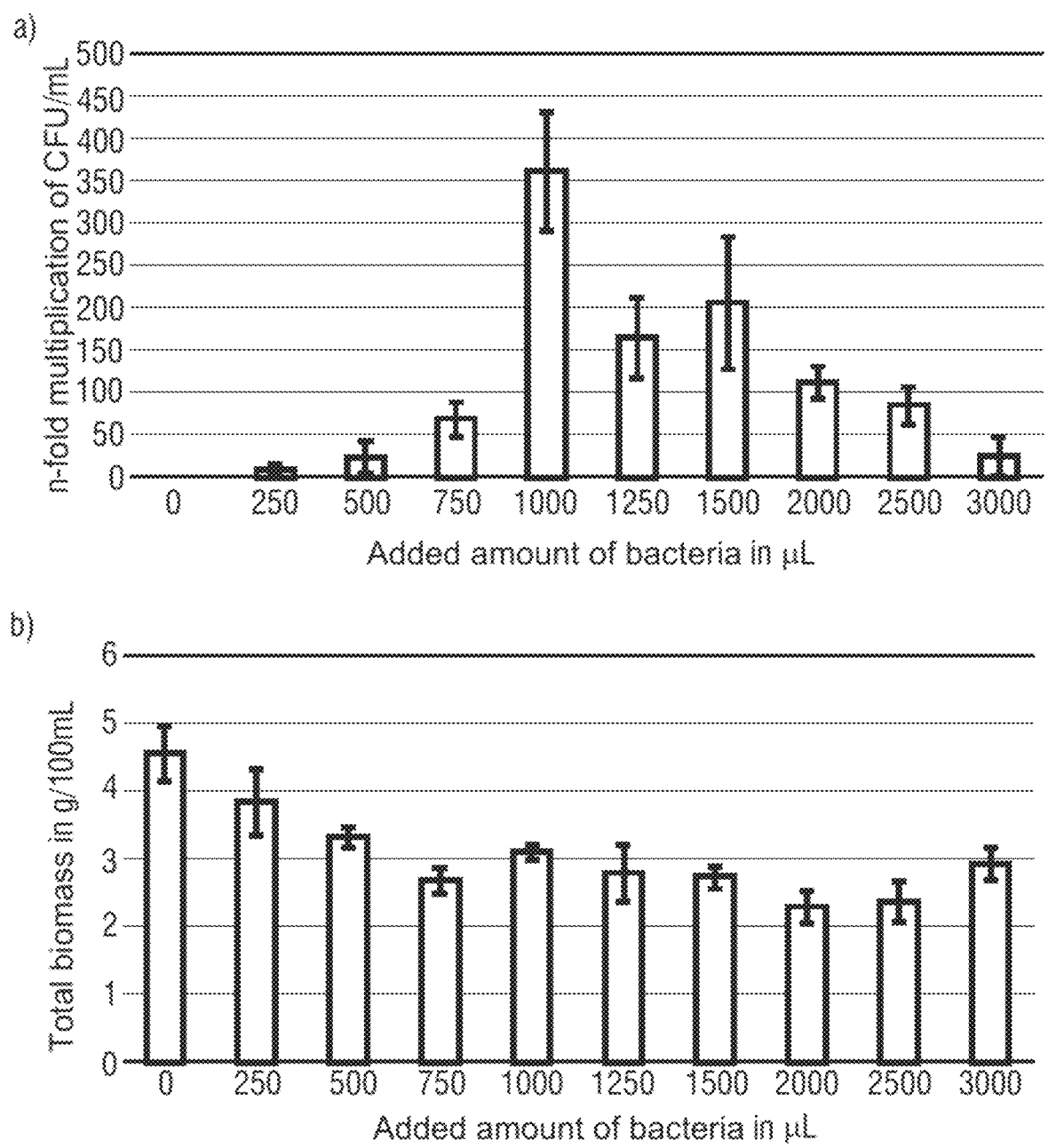
FIG. 2a shows the growth of bacteria of a bacteria culture consisting of *P. freudenreichii* subspecies *shermanii* and *P. freudenreichii* subspecies *freudenreichii* as n-fold increase of the initial added amount in CFU/mL.
FIG. 2b shows the growth of bacteria of a bacteria culture consisting of *P. freudenreichii* subspecies *shermanii* and *P. freudenreichii* subspecies *freudenreichii* as the total biomass including *Pleurotus sapidus* (PSA) in g/100 ml determined by weighing the harvested and dried biomass.

In further experiments, 10 ml PSA pre-culture in M1 medium and 10% isomaltulose molasses was aerobically incubated for 7 days, shaking (150 rpm) at 24° C. Subsequently, different amounts of bacteria pre-culture (approx. 6*10$^9$ CFU/ml) consisting of *P. shermanii* and *P. freudenreichii* were added as well as switching to anaerobe conditions and a temperature shift to 30° C. and further incubation for 48 h were carried out. This variant, upon addition of 1 mL bacteria pre-culture, resulted in the greatest growth of bacteria and satisfying growth of fungus (determined optically) and sufficient total biomass. The control reaction with 0 µl bacteria pre-culture added and shifting the temperature to 30° C. yielded a total biomass, i.e. Basidiomycota biomass, of approx. 46 g/L, based on the dry mass (cf. FIG. 2).

Figure 3:
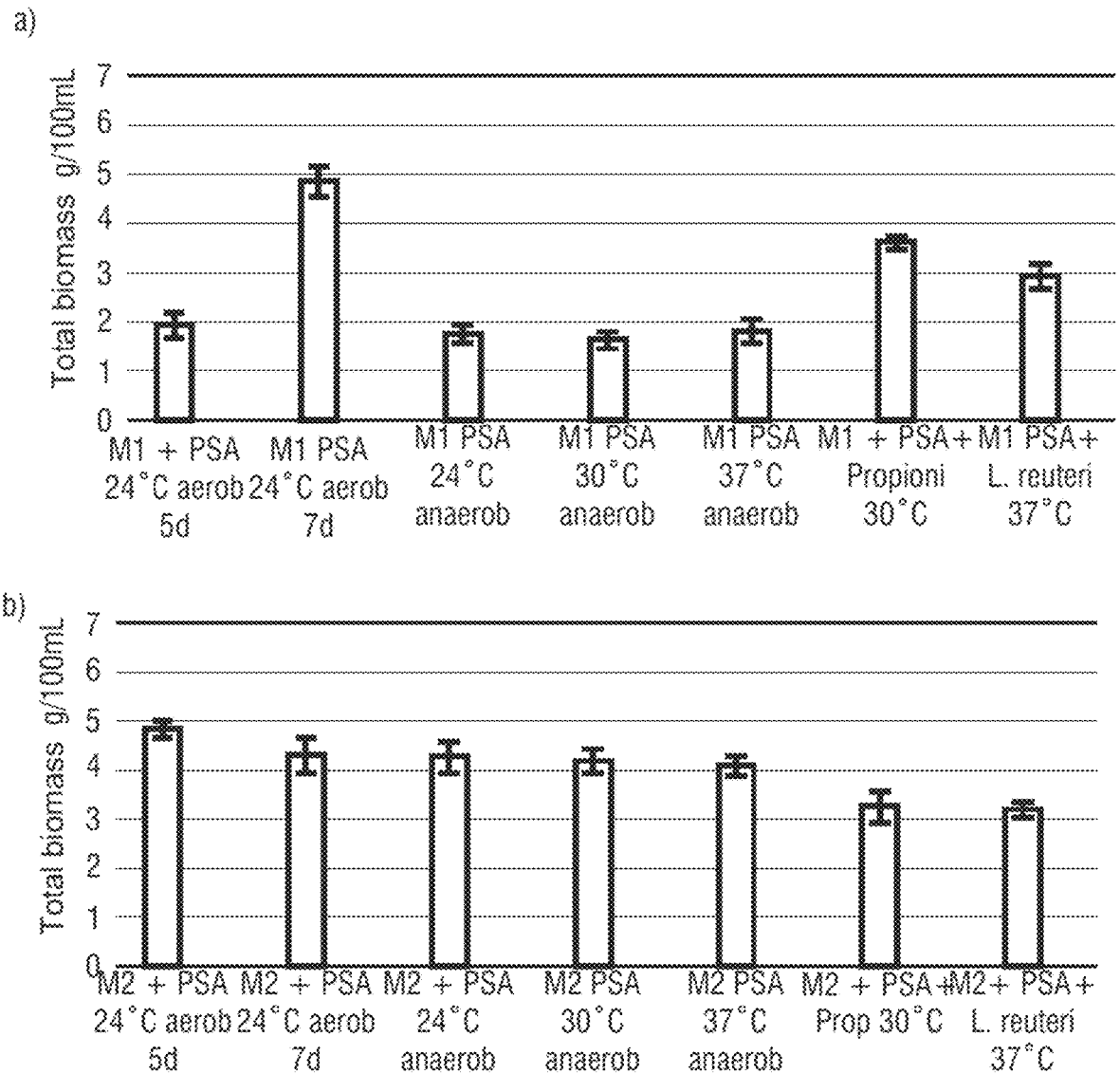
FIG. 3a shows the total biomass in g/100 ml of *Pleurotus sapidus* (PSA) cultures or co-cultures of PSA and vitamin B12-producing bacteria on M1-medium, determined by weighing the harvested and dried biomass.
FIG. 3b shows the total biomass in g/100 ml of *Pleurotus sapidus* (PSA) cultures or co-cultures of PSA and vitamin B12-producing bacteria on M1-medium M2-medium, determined by weighing the harvested and dried biomass.

In a further series of experiments, the total biomasses of cultures of PSA as well as co-cultures of PSA and vitamin B12-producing bacterial strains, which were cultivated in different minimal media with isomaltulose molasses, were determined. Hereby, 10 ml PSA pre-culture were incubated for 5 days or 7 days in 90 ml M1 or M2 medium, each with 10% isomaltulose molasses added, aerobically at 24° C. and the total biomass was determined after harvest (cf. FIGS. 3*a*) and *b*), each 1. and 2. column). For further batches, the cultivation conditions were switched from aerobe to anaerobe after the 5-day incubation and incubation was continued at different temperature for 48 h (24° C., 30° C. or 37° C., cf. FIGS. 3*a*) and *b*), each 3. to 5. column). Subsequently, also the weight of the total biomass was determined. To further batches, after the 5-day incubation, bacteria pre-cultures (approx. 6*10$^9$ CFU/ml) consisting of *P. shermanii* and *P. freudenreichii* or *L. reuteri* were added, it was switched to anaerobe conditions and a temperature shift to 30° C. or 37° C. was performed, and for 48 h cultivated under these conditions (cf. FIGS. 3*a*) and *b*), each 6. to 7. column). Subsequently, the determination of the total biomass was carried out as for all batches. In total, cultures in M2 medium showed over a period of 5 days a higher fungus biomass than cultures in M1 medium. However, the biomass could be further increased within 7 days incubation in M1 medium, while this was not the case for the M2 medium. Thus, both in the M1 as well as the M2 medium, total biomasses of up to 49 g/100 ml, based on the dry mass, could be achieved by cultivation of the Basidiomycota prior to addition of the bacteria species.

Figure 4:
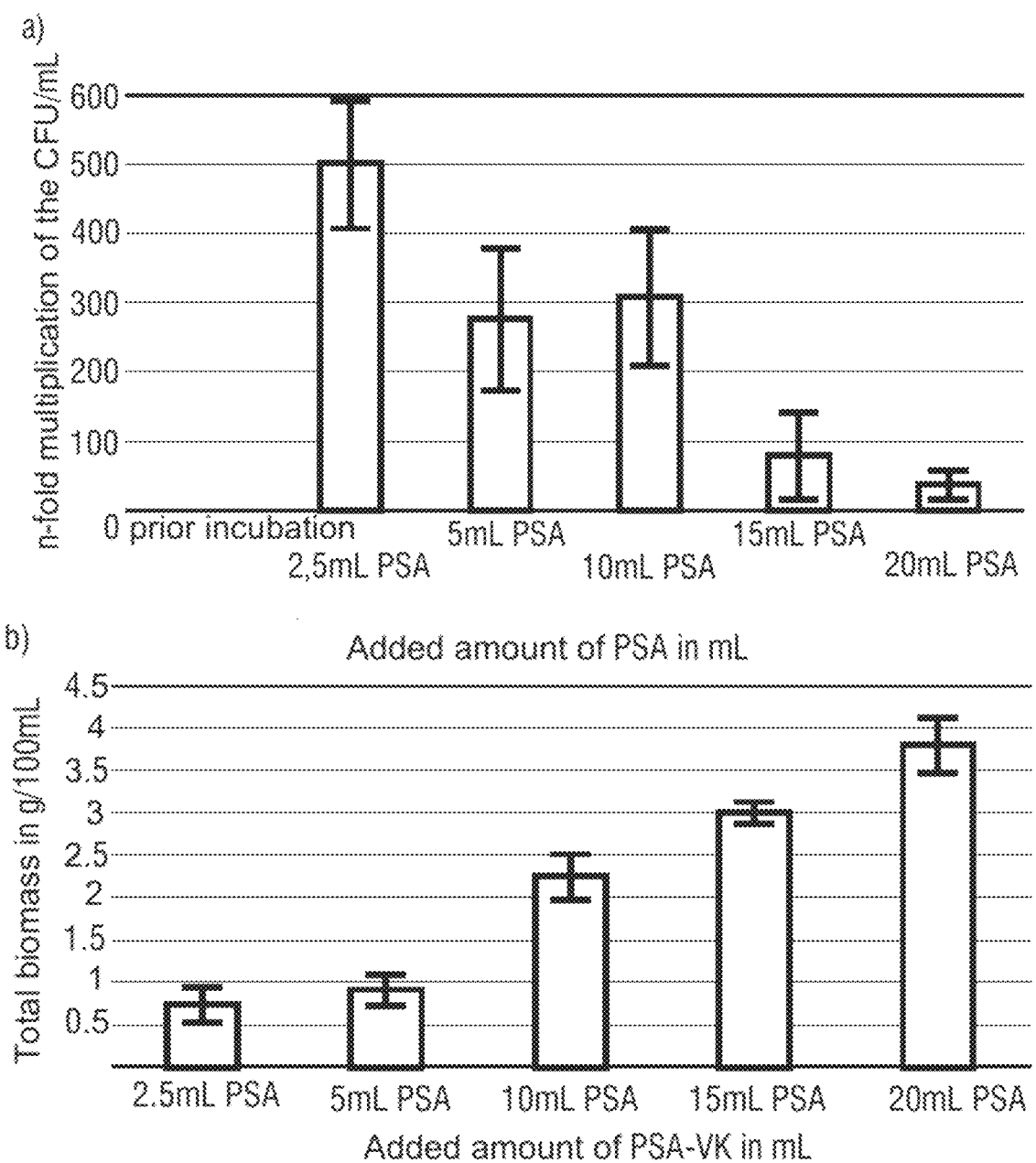
FIG. 4a shows the growth of bacteria of a bacteria culture consisting of *P. shermanii* and *P. freudenreichii* as n-fold increase of the initial added amount in CFU/mL.
FIG. 4b shows the growth of bacteria of a bacteria culture consisting of *P. shermanii* and *P. freudenreichii* as the total biomass including *Pleurotus sapidus* (PSA) in g/100 ml determined by weighing the harvested and dried biomass.

Further, use of different amounts of PSA fungus pre-culture at unvaried bacteria amounts (1 ml, approx. 6*10$^9$ CFU/ml) were tested. For this, 10 ml PSA pre-culture were incubated aerobically for 7 days in 90 ml M1 medium, with 10% isomaltulose molasses added. Subsequently, 1 ml of a pre-culture propionibacteria (approx. 6*10$^9$ CFU/ml) was added, it was switched to anaerobe conditions and a temperature shift to 30° C. was performed as well as cultivated for 48 h under these conditions (cf. FIG. 4). Hereby, it could be shown that increasing amounts of PSA lead to higher total biomass but inhibit the growth of bacteria.

Figure 5:
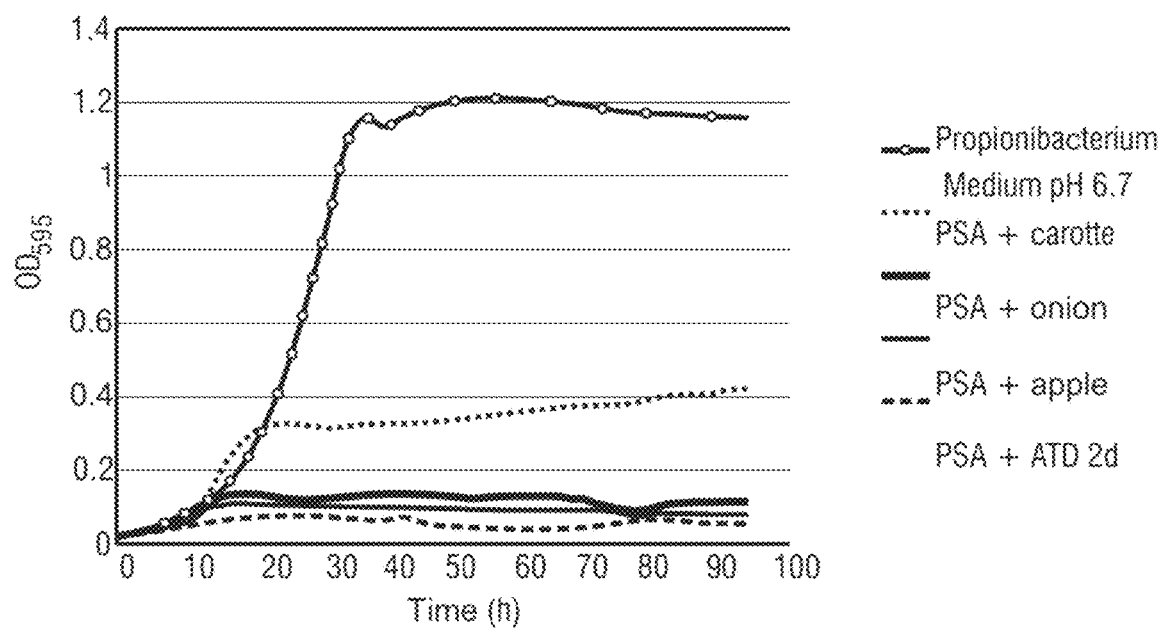
FIG. 5 shows the growth of *P. freudenreichii* subspecies *shermanii* on optimum medium and on *Pleurotus sapidus* (PSA) culture supernatants.
Figure 6:
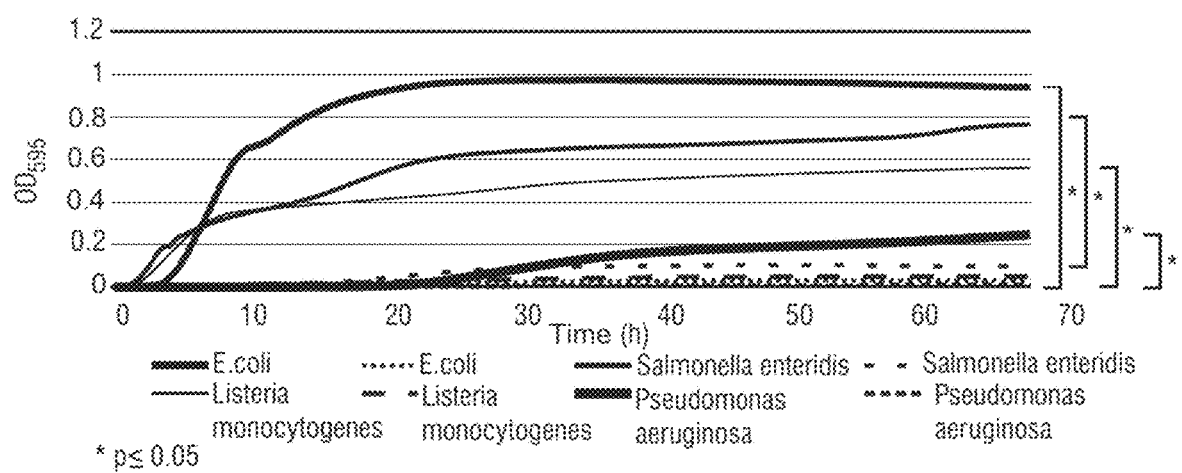
FIG. 6 shows the growth of *E. coli, L. monocytogenes, S. enteritidis enteritis*, and *P. aeruginosa* on optimum media and on *Pleurotus sapidus* (PSA) culture supernatants.

In a further series of experiments, the growth of bacteria on *Pleurotus sapidus* (PSA) supernatants was determined (cf. FIG. 5). For this, PSA was cultivated on different agricultural tributaries and harvested. The culture on isomaltulose was kept in M2 medium for 5 days prior to harvest, the cultures on carotte pomace, onion pomace and apple pomace were kept in M1 medium over 4 days prior to harvest. In a further batch, the culture was kept in M1 medium on apple pomace for 2 days prior to harvest (cf. FIG. 5, "ATD 2d"). The media used for cultivation were, subsequent to the harvest of the fungus mycelium, used for cultivation of *P. freudenreichii* supspec. *shermanii*. In a control experiment, *P. freudenreichii* supspec. *shermanii* was cultivated on optimum medium (propioni bacteria medium). Hereby, it turned out that *P. freudenreichii* supspec. *shermanii* hardly grew on PSA culture supernatants. Also, further bacteria species showed only very little growth on PSA culture supernatants based on apple pomace as agricultural tributary after 5 days cultivation of the PSA mycelium and subsequent harvest (cf. FIG. 6, dotted lines) compared to growth on the corresponding optimum medium (cf. FIG. 6, straight lines).

Figure 7:
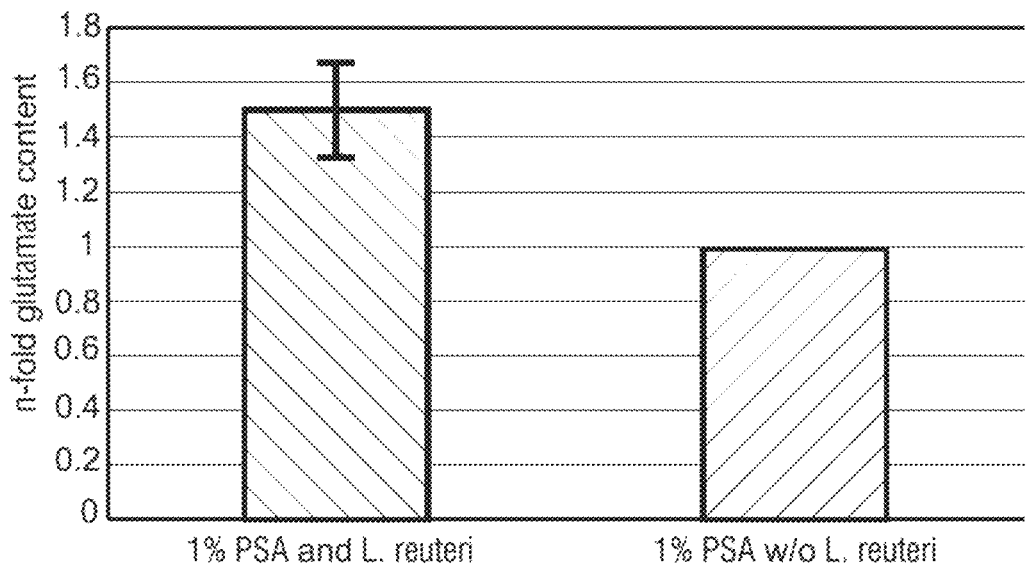
FIG. 7 shows the increase in glutamate content in *Pleurotus sapidus* (PSA)-mycelium by cultivation with *L. reuteri*.

These results show that, specifically the form of co-cultivation with Basidiomycota, leads to particularly high bacteria division rates. Surprisingly, significantly lower bacteria division rates are achieved for the cultivation of Basidiomycota supernatants, i.e. on used media without Basidiomycota. Already after 2 days of PSA cultivation on apple pomace, the used media significantly inhibits growth of *P. freudenreichii* supspec. *shermanii* (cf. FIG. 5), whereas a significant bacteria growth is achieved in the co-culture also after 5 days of PSA cultivation prior addition of the bacteria (cf. FIG. 2-4).

mycelium lead to the detection of an increased conversion of glutamine after fermentation by *L. reuteri*. Subsequent a triple determination, an average increase in glutamate content of 52% was determined (cf. FIG. 7).

Example 4

Determination of Vitamin B12 in Co-Cultures of *Pleurotus sapidus* and Vitamin B12-Producing Bacterial Strains as Well as in Bacteria Cultures Only 10 ml *Pleurotus sapidus* (PSA) pre-culture were incubated in 90 ml M1 medium, with 10% isomaltulose molasses added, for 7 days shaking at 24° C. Subsequently, 1 ml *L. reuteri* or *P. freudenreichii* supspec. *freudenreichii* and *shermanii* were added (1 ml, approx. $6*10^9$ CFU/ml) and incubation was continued for 48 h at 30° C. or 37° C. under anaerobe conditions. The cultures were centrifuged subsequent to incubation, the pellet was dissolved in $H_2O$ and sonicated for 10 min at 60% amplitude (1 min pulse, 1 min pause) together with glass balls in a ratio of 1:2 (glass balls/culture). Subsequently, the conversion of all cobalamins was carried out by addition of 10% potassium cyanide solution with a final concentration of 2%. After 10 min incubation at room temperature another centrifugation was carried out and the supernatant was analyzed by means of ELISA for the presence of cyanocobalamin.

Figure 8:
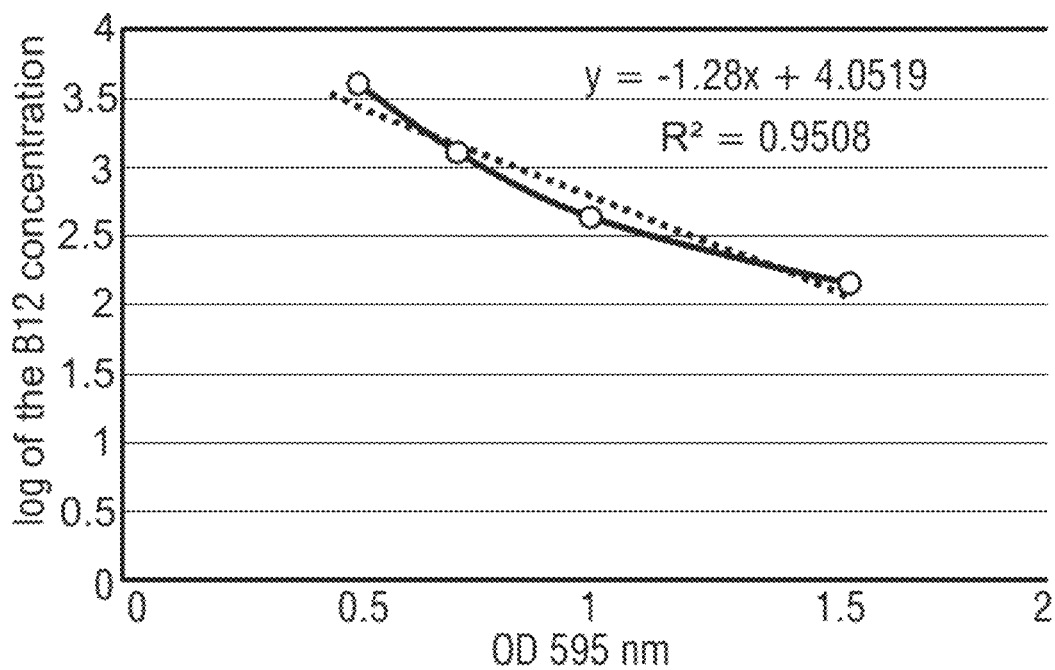
FIG. 8 shows a vitamin B12 standard curve of the used ELISA assay for the determination of vitamin B12 in the co-cultures.

For the calculation of the amounts of vitamin B12 contained in the cultures, a standard curve of defined amounts of cyanocobalamin was prepared (cf. FIG. 8), which was used for determining the amounts of vitamin B12 contained in the cultures.

In the following table, the present contents of vitamin B12 from the co-cultures are illustrated. Assuming that in the final product, e.g. vegan bratwurst, 25 g protein a used per 1 kg, the vitamin B12 content per 100 g bratwurst is about 0.3 µg.

TABLE 3

Vitamin B12 content in co-cultures of Basidiomycota and bacteria.

| Organisms of the co-culture | OD at 450 nm | Log (Vit. B12-conc.) | Conc. of Vit. B12 (pg/ml) | µg Vit. B12 in 100 ml co-culture | Amount of co-culture for covering the daily requirement of Vit B12 (l) | Amount dry mass for covering the daily requirement of Vit B12 (g) |
|---|---|---|---|---|---|---|
| PSA, *L. reuteri* | 0.229 | 3.76 | 5738.25 | 0.057 | 5.22 | 29.8 |
| PSA + *Propiobacterium freudenreichii* sups. *freudenreichii a. shermanii* | 0.2521 | 3.73 | 5360.58 | 0.107 | 2.79 | 15.98 |

Example 3

Conversion of the Glutamine Contained in the *Pleurotus sapidus* Mycelium into Glutamate by *L. reuteri*

1% lyophilized fungus mycelium was incubated with and without *L. reuteri* overnight at 37° C. and on the next day, the glutamate proportion was determined after digestion. The determination of the glutamate content on lyophilized, beforehand enzymatically digested *Pleurotus sapidus* (PSA)

The vitamin B12 content in the bacteria cultures without Basidiomycota was also determined and was significantly higher (cf. Tab. 4). For this, the bacteria cultures were either anaerobically cultivated for 2 days and subsequently for 24 h aerobically or 3 days anaerobically at the corresponding optimum temperature of the bacterial strain. The bacteria content was approx. $6*10^9$ CFU/ml.

However, such a production would be significantly more laborious and more prone to contamination, for which reason the approach of the co-culture is pursued.

TABLE 4

Vitamin B12 content in differently cultured cultures of vitamin B12-producing bacterial strains.

| Bacterium | Cultivation | Conc. Vit. B12 (ng/ml) in culture | Amount of culture for covering the daily requirement of Vit B12 | Conc. Vit. B12 in the pellet of bacteria(μg/100 g) | Amount of pellet for covering the daily requirement (g) |
|---|---|---|---|---|---|
| *L. reuteri* | 2 d anaerob, 1 d aerob | 12.4 | 4.03 | n.a. | n.a |
| *L. reuteri* | 3 d anaerob | 10.09 | 7.42 | 3 | 100 |
| *P. freudenreichii* subs. *freudenreichii* and *shermanii* | 2 d anaerob, 1 d aerob | 12.69 | 3.93 | n.a. | n.a. |
| *P. freudenreichii* subs. *freudenreichii* and *shermanii* | 3 d anaerob | 13.99 | 5.35 | 3.23 | 92.88 |

Example 5

Figure 9:
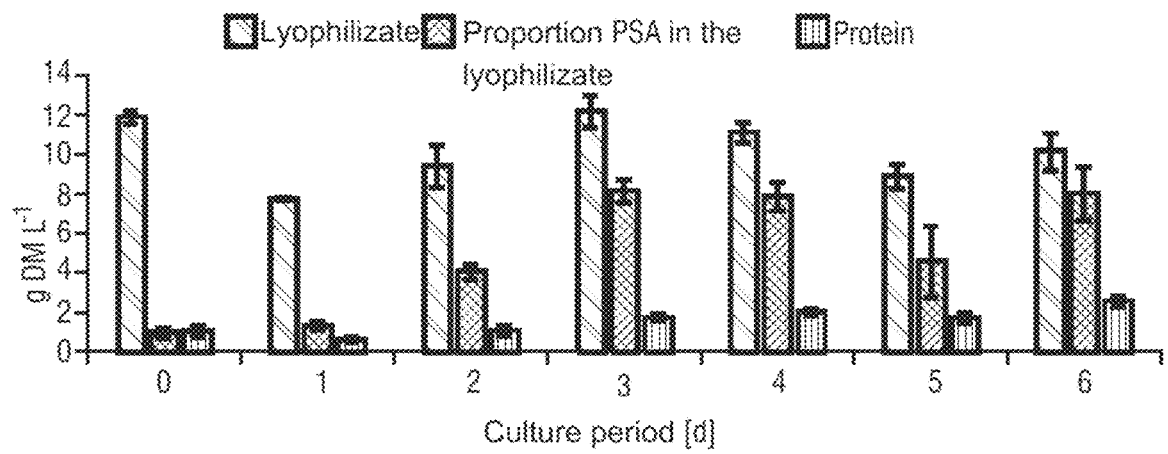
FIG. 9 shows the quantification of the *Pleurotus sapidus* (PSA) proportion in the lyophilizate, cultivated on the agricultural tributary apple pomace, determined via the ergosterol-content (highlighted in black); the quantification of the protein content was performed according to the method of Kjeldahl (highlighted in grey).
Figure 10:
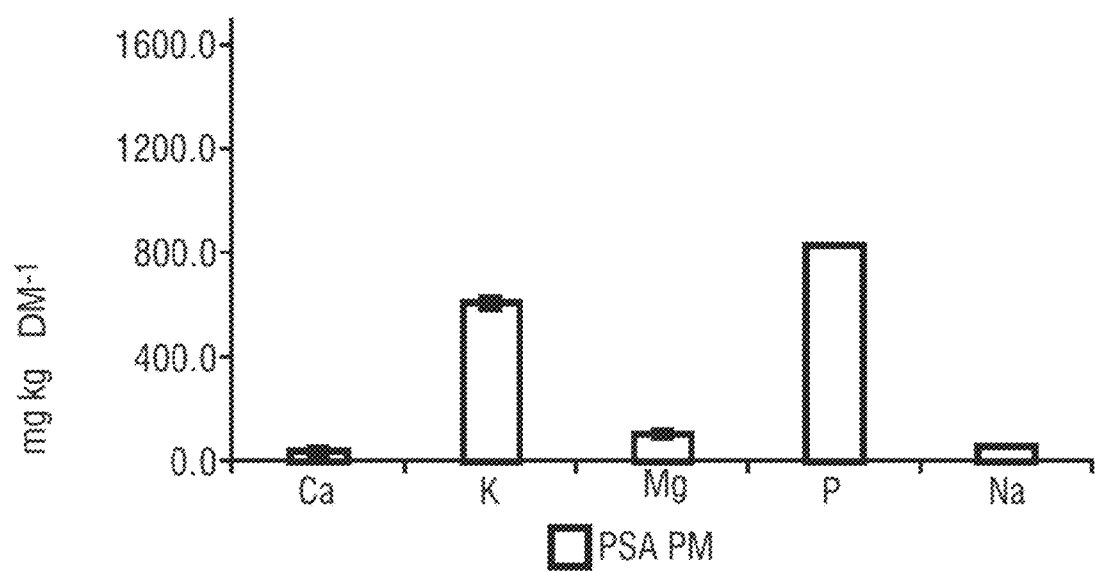
FIG. 10 shows the bulk elements of *Pleurotus sapidus* (PSA), cultivated on isomaltulose molasses (PM).
Figure 11:
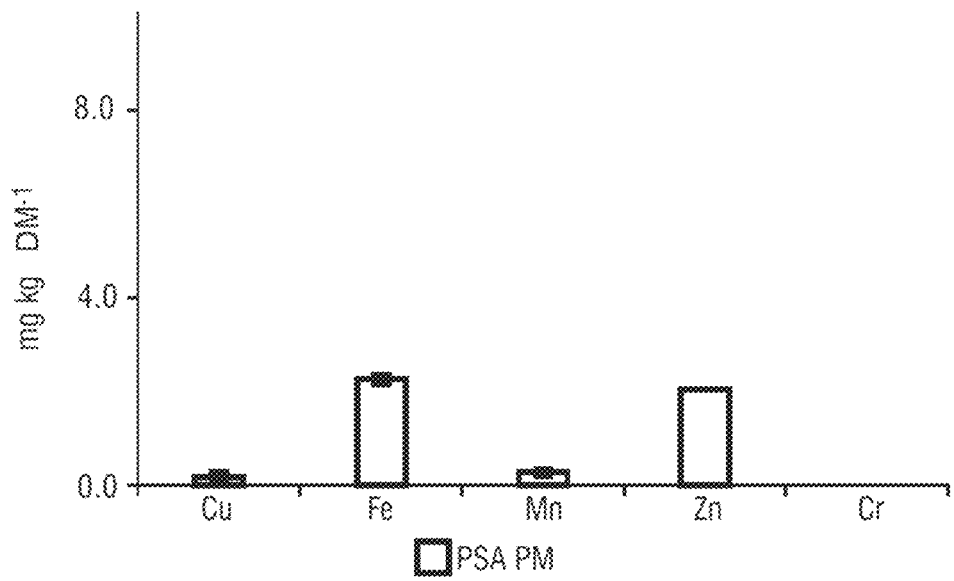
FIG. 11 shows the essential trace elements of *Pleurotus sapidus* (PSA), cultivated on isomaltulose molasses (PM).
Figure 12:
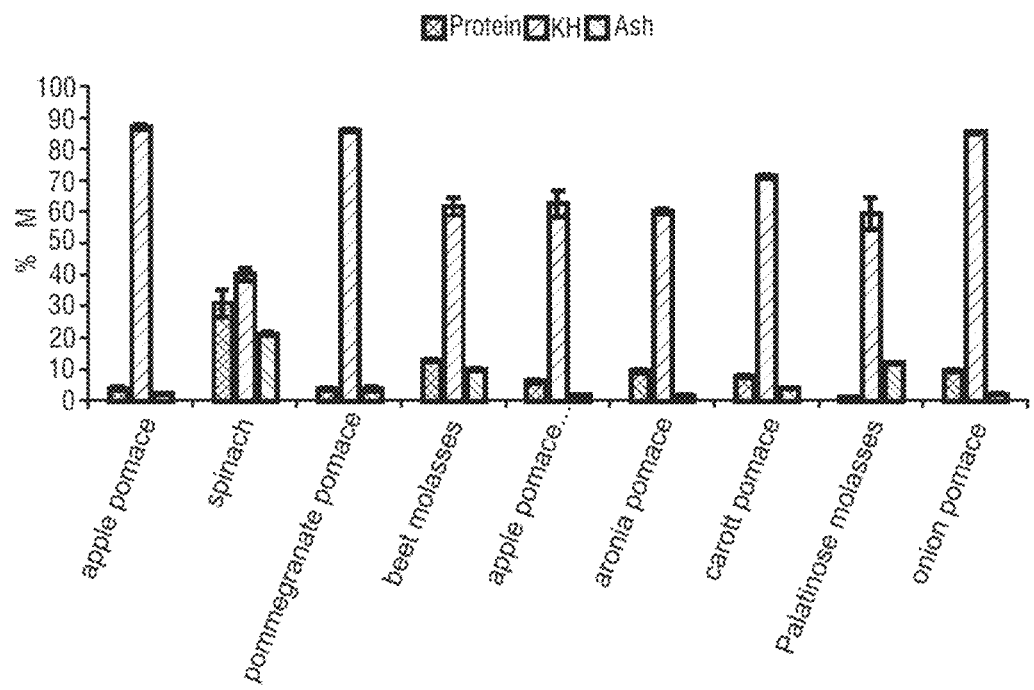
FIG. 12 shows the composition of the substrate of the different agricultural tributaries used for cultivation.

Quantification of the Fungus Proportion in the Lyophilizate Via Ergosterol Exemplified by the Cultivation of PSA on Apple Pomace The protein content and the proportion of *Pleurotus sapidus* (PSA) in the total biomass was measured for 6 days. Hereby, the proportion of PSA was determined via ergosterol measurement. The proportion of PSA as well as the protein content increase with the culture period. When determining the total weight of the mycelium, from day 4, a slight decreasing tendency was observable (cf. FIG. 9). The proportion of PSA in the lyophilizate was approx. 80% at the time of harvest.

Example 6

Results of the Determination of Mineral Nutrients and Sugars in PSA Mycelium, Cultivated on Isomaltulose Molasses as Well as Illustration of the Substrate Composition The conversion of glucose and fructose from the isomaltulose molasses (Palatinose molasses/PM) substrate by *Pleurotus sapidus* (PSA) as well as from the carotte pomace (K) by *Lentinula edodes* (LED) was quantified (cf. Tab. 5).

TABLE 5

Conversion of D-glucose and D-fructose from the substrate.

| Basidiomycota species | Conversion D-glucose from the substrate [%] | Conversion D-fructose from the substrate [%] |
|---|---|---|
| PSA - PM | 75.2 ± 0.2 | 68.1 ± 0.3 |
| LED - K | 89.6 ± 0.3 | 98.9 ± 0.0 |

The amount of glucose and fructose in the fungus mycelium as well as in the used substrate was determined (cf. Tab. 6).

TABLE 6

Determination of D-glucose and D-fructose in the fungus mycelium and substrate.

| Sample | D-glucose [g (100 g DM)$^{-1}$] | D-fructose [g (100 g DM)$^{-1}$] |
|---|---|---|
| PSA PM | 4.9 ± 0.0 | 9.4 ± 0.2 |
| Isomaltulose molasses | 12.4 ± 1.7 | 19.0 ± 2.1 |
| LED K | 0.3 ± 0.0 | 0.1 ± 0.0 |
| Carrot pomace | 2.4 ± 0.1 | 7.0 ± 0.0 |

TABLE 7

Composition of saccharides and heavy metal contamination in *Pleurotus sapidus* (PSA) cultivated on apple pomace (ATD), in the residue substrate ATD as well as saccharides composition in PSA cultivated on isomaltulose molasses (PM).

| PSA ATD | Concentration [g/(100 g DM)$^{-1}$] | ATD substrate | Concentration [g/(100 g TM)$^{-1}$] |
|---|---|---|---|
| Chitin | 6.54 ± 1.79 | | |
| Total glucan | 9.22 ± 0.16 | Total glucan | 4.39 ± 0.97 |
| Beta-glucan | 5.59 | Beta-glucan | 3.42 |
| Alpha-glucan | 3.64 ± 0.09 | Alpha-glucan | 0.97 ± 0.05 |
| Glucose | 0.55 ± 0.02 | Glucose | 1.5 ± 0 |
| Fructose | 0.07 ± 0.01 | Fructose | 5.15 ± 0.02 |
| Saccharose | 0.34 ± 0.01 | Saccharose | 0.32 ± 0.06 |

| PSA ATD | Concentration [μg/(kg DM$^{-1}$] | ATD substrate | Concentration [μg/(kg DM$^{-1}$] |
|---|---|---|---|
| Lead | n.d. | Lead | n.d. |
| Cadmium | 13.3 ± 1.9 | Cadmium | 12.3 ± 1.9 |
| Mercury | n.d. | Mercury | n.d. |

| PSA PM | Konzentration [g/(100 g DM$^{-1}$] |
|---|---|
| Alpha-glucan | 6.1 |
| Beta-glucan | 18.7 |
| Total glucan | 24.8 |

Example 7

Amino Acid Profile

Figure 16:
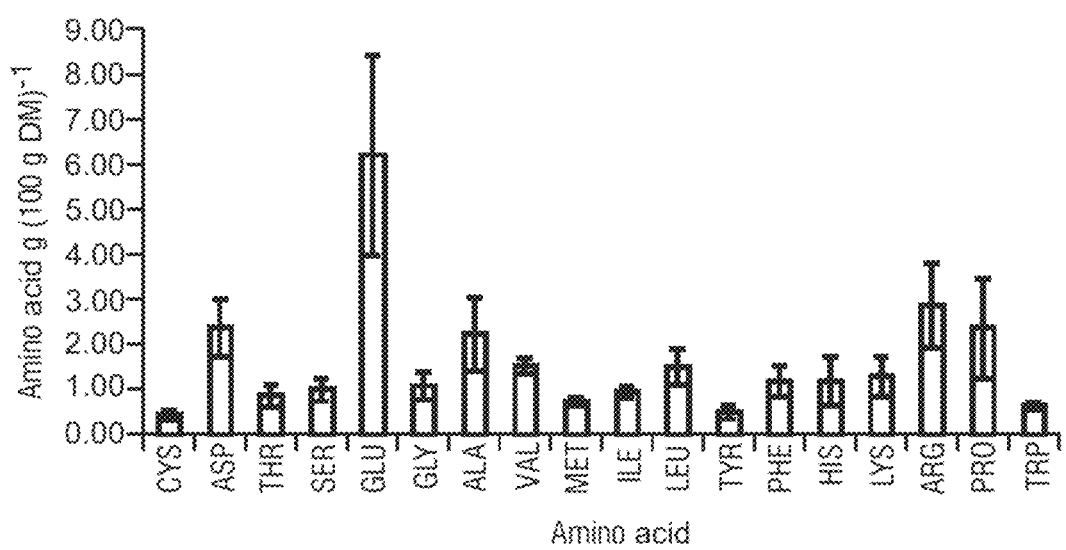
FIG. 16 shows the quantification of the single amino acids from *Pleurotus sapidus* (PSA) on isomaltulose molasses.

The total amino acid content of 29.41 g (100 g DM)$^{-1}$ was calculated as sum of the single amino acids. When comparing this content to the total crude protein content according to Kjeldahl (27.41 g (100 g DM)$^{-1}$), these values correlate well with each other. In sum, an amino acid spectrum of in total 18 amino acids results, amongst them the 8 essential as well as both the semi-essential amino acids arginine and histidine (cf. FIG. 16).

Example 8

Vitamin D2 Production

Figure 13:
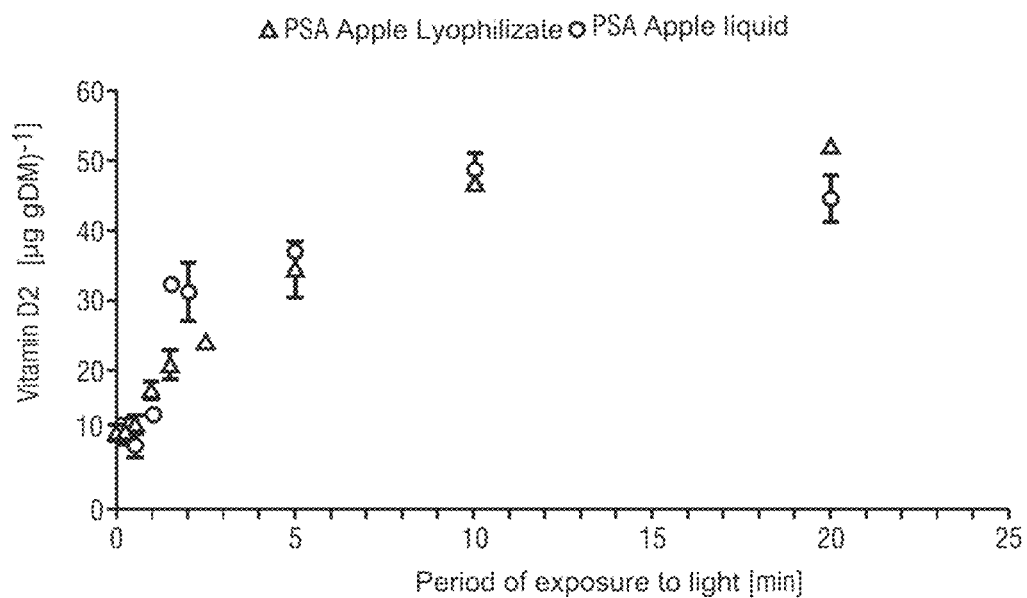
FIG. 13 shows the vitamin D2 concentration of a *Pleurotus sapidus* (PSA) culture on apple pomace after irradiation of the lyophilizate and the liquid submerged culture, respectively, which was subsequently lyophilized.

In two series of experiments it was tested, whether there are differences in the irradiation of the already lyophilized fungus mycelium in comparison to the irradiation of the entire submerged culture in liquid state. The diameter of the crystallization dishes, in which light exposure was performed, was 9.5 cm in case of the lyophilizate (sample height: 0.8 cm) and 19.8 cm for the light exposure of the liquid culture (sample height: 1 cm). Already an exposure of only a few seconds was sufficient to produce so much vitamin D2 that the daily requirement of 5 μg is already exceeded by the consumption of 1 g dry fungus mycelium (cf. FIG. 13). Thus, for the future production, mycelium exposed and not exposed to light may be mixed to not exceed the daily requirement of vitamin D2. The irradiation of lyophilizate, which stems from the cultivation of PSA on isomaltulose and 10 min with UV light at a distance from the lamp of 10 cm, resulted in a vitamin D2 content of 0.2 μg/g dry mass.

Example 9

Decrease of the RNA Content

By heat treatment of a PSA culture on isomaltulose molasses at the end of the incubation period, the RNA content could be significantly decreased in comparison with the untreated samples. Specifically, the combination of 40 minutes at 40° C. and 20 minutes at 70° C. lead to the significant decrease of the total RNA (18 S and 28 S RNA). Thus, a health benefit of the product can be achieved, which is particularly relevant for risk groups amongst the consumers (cf. FIG. 14).

Example 10

Techno Functional Examinations

The following abbreviation are used in the following: "g" dried pomace (otherwise moist pomace); "[number] d"=number of days of the cultivation.

Further, the following abbreviations are used for the Basidiomycota strains, the tributaries as well as the media:

TABLE 8

Used strains and tributaries.

| Strain | By-product stream |
|---|---|
| AAE (*Agrocybe aegerita*) | KTD (carotte pomace Döhler) |
| LED (*Lentinula edodes*) | KT (carotte pomace) |
| LSU (*Laetiporus sulphureus*) | AT (apple pomace) |
| PSA (*Pleurotus sapidus*) | ZT (onion pomace) |
| PEO (*Pleurotus roseus*) | GA (pomegranate pomace) |
| SRU (*Stropharia rugosoannulata*) | Aro (aronia pomace) |
| WCO (*Wolfiporia cocos*) | BS (spinach) |
| | PM (isomaltulose molasses) |

TABLE 9

Liquid media used for media optimization.

| | Na-Aspartate [g L$^{-1}$] | NH$_4$NO$_3$ [g L$^{-1}$] | (NH$_4$)$_2$SO$_4$ [g L$^{-1}$] | KH$_2$PO$_4$ [g L$^{-1}$] | MgSO$_4$ [g L$^{-1}$] | SE-Sol. [mL L$^{-1}$] |
|---|---|---|---|---|---|---|
| M1 | 6.2 | 2.4 | — | 1.5 | 0.5 | 1.0 |
| JA1 | 3.1 | 2.4 | — | 1.5 | 0.5 | 1.0 |
| JA2.1 | 6.2 | — | 4.0 | 1.5 | 0.5 | 1.0 |
| JA2.2 | 6.2 | — | 2.4 | 1.5 | 0.5 | 1.0 |
| JA3 | 6.2 | 2.4 | — | 0.5 | 0.5 | 1.0 |
| JA4 | 3.1 | — | 2.4 | 0.5 | 0.5 | 1.0 |
| DI H$_2$O with SE | — | — | — | — | — | 1.0 |
| DI H$_2$O | — | — | — | — | — | — |

SE: trace element solution, Na-Aspartate: L-aspartic acid monosodium salt monohydrate.

TABLE 10

Liquid media used for media optimization..

| | Yeast extract [g L$^{-1}$] | Pepton (Soy) [g L$^{-1}$] | NH$_4$NO$_3$ [g L$^{-1}$] | (NH$_4$)$_2$SO$_4$ [g L$^{-1}$] | KH$_2$PO$_4$ [g L$^{-1}$] | MgSO$_4$ [g L$^{-1}$] | SE-Sol. [mL L$^{-1}$] |
|---|---|---|---|---|---|---|---|
| M2 | 3.0 | — | — | — | 1.5 | 0.5 | 1.0 |
| M2a | 3.0 | — | 2.4 | — | 1.5 | 0.5 | 1.0 |
| M2b | 3.0 | — | — | — | 0.5 | 0.5 | 1.0 |
| M3 | — | 3.0 | — | — | 1.5 | 0.5 | 1.0 |
| M3a | 3.0 | 3.0 | — | — | 1.5 | 0.5 | 1.0 |
| M3b | — | 3.0 | — | — | 0.5 | 0.5 | 1.0 |

SE: trace element solution

Water Binding Capacity:

The samples LSU_KTD_16T_M1_20.8.15, LSU_KTD_16T_M2_20.8.15, PSA_AT_M1_G_5.8.15, PSA_KT_G_5.8.15, PSA_KT_G_5.8.15_II, PSA_KTD_16T_M2_20.8.15 and PSA_ZT_20.2.15 all have a high water binding capacity. The influence of the agricultural by-product stream, however, is hereby not to be underestimated, because specifically fibers from carrots, apples or onions have high capillary forces, which also have a high water binding capacity. Considering the Basidomycete *Pleurotus sapidus* on isomaltulose molasses (PSA_PM), no functionality can be expected from the isomaltulose molasses used. The properties of mycelium from PSA_PM can be compared with pea protein isolate.

TABLE 11

Water binding capacities.

| Name | WBC/ Protein*100 | WBC [mL/g] | Protein [%] |
|---|---|---|---|
| 112541_peaproteinisolate | 3.50 | 3.2 | 90.1 |
| 113764_soyconcentrate | 5.87 | 4.1 | 69.8 |
| 118770_soyisolate | 7.45 | 6.7 | 90.2 |
| AAE_AT_total6 | 30.45 | 5.1 | 16.7 |
| AAE_ATD_G_10.8.15 | 31.10 | 5.8 | 18.6 |
| AAE_ATD_G_10.8.15_II | 35.73 | 6.6 | 18.6 |
| AAE_BS_total2 | 12.37 | 3.2 | 26.1 |
| AAE_GA_total7 | 27.56 | 5.1 | 18.6 |
| AAE_KTD_16T_M1_20.8.15 | 23.04 | 5.0 | 21.8 |
| AAE_KTD_16T_M2_20.8.15 | 28.42 | 5.5 | 19.2 |
| AAE_P100_M1_16.2.15 | 8.43 | 1.1 | 13.3 |
| LED_ATD_G_10.8.15 | 18.58 | 3.8 | 20.4 |
| LED_ATD_G_10.8.15_II | 22.20 | 4.5 | 20.4 |
| LED_GA_16.4.15 | 19.94 | 3.2 | 16.3 |
| LED_GA_16.4.15_II | 21.50 | 3.5 | 16.3 |
| LED_KTD_6T_M1_20.8.15 | 12.63 | 3.4 | 27.2 |
| LED_KTD_M1_8.15 | 14.99 | 4.0 | 27.0 |
| LED_P100_16T_M2_30.3.15 | 16.39 | 3.9 | 24.0 |
| LSU_AT_total4 | 34.31 | 5.3 | 15.5 |
| LSU_KTD_16T_M1_20.8.15 | 76.15 | 7.0 | 9.1 |
| LSU_KTD_16T_M2_20.8.15 | 83.58 | 7.3 | 8.8 |
| PSA_Aro_G_18.8.15 | 35.67 | 4.2 | 11.6 |
| PSA_Aro_G_18.8.15_II | 30.59 | 3.6 | 11.6 |
| PSA_AT_total1 | 22.670 | 4.5 | 20.0 |
| PSA_AT_M1_G_5.8.15 | 34.37 | 7.1 | 20.7 |
| PSA_BS1_total 9 | 21.10 | 5.9 | 28.0 |
| PSA_BS2_31.3.15 | 13.97 | 3.9 | 28.0 |
| PSA_GA_total3 | 29.79 | 3.3 | 11.1 |
| PSA_KT_G_5.8.15 | 28.91 | 7.3 | 25.1 |
| PSA_KT_G_5.8.15_II | 29.28 | 7.3 | 25.1 |
| PSA_KTD_16T_M2_20.8.15 | 23.29 | 7.5 | 32.1 |
| PSA_KTD_3T_M2b_29.9.15 | 13.20 | 3.1 | 23.5 |
| PSA_KTD_4T_M2_14.9.15 | 7.24 | 2.2 | 30.7 |
| PSA_KTD_6T_M2a_14.9.15 | 9.79 | 2.1 | 21.9 |
| PSA_KTD_6T_M3_14.9.15 | 10.82 | 2.2 | 20.2 |
| PSA_KTD_6T_M3a_21.9.15 | 10.51 | 1.9 | 18.5 |
| PSA_KTD_9T_M3b_21.9.15 | 19.29 | 2.4 | 12.4 |
| PSA_P100_M1M2_21.8.15 | 12.64 | 2.5 | 20.1 |
| PSA_PM_M2 | 11.560 | 2.7 | 23.8 |
| PSA_ZT_20.2.15 | 71.70 | 7.8 | 10.9 |
| PSA_ZT_24.11.14 | 17.31 | 4.9 | 28.4 |
| SRU_BS_total5 | 14.13 | 4.8 | 34.0 |
| SRU_GA_total8 | 59.40 | 4.2 | 7.0 |
| WCO_Aro_G_18.8.15 | 27.15 | 3.5 | 12.9 |
| WCO_Aro_G_18.8.15_II | 26.31 | 3.4 | 12.9 |
| WCO_KTD_24T_M1_20.8.15 | 40.77 | 5.4 | 13.2 |
| WCO_ZT_24.11.14 | 43.81 | 6.1 | 14.0 |
| WCO_ZT_25.11.14_II | 25.66 | 3.6 | 14.0 |

Oil Binding Capacity:

Some agricultural tributaries bind more oil than others (caused by the fiber proportion). Comparing the water binding capacity of *Pleurotus sapidus* on isomaltulose molasses (PSA_PM) to plant proteins, the Basidiomycota mycelium has a significantly higher oil binding capacity. This functionality may be explained by the formation of β-glucans and chitin by the basidiomycete.

TABLE 12

Oil binding capacity.

| | OBC/ Protein*100 | OBC [ml/g] | Protein [%] |
|---|---|---|---|
| 112541_peaproteinisolate | 1.09 | 0.9 | 90.1 |
| 113764_soyconcentrate | 2.06 | 1.1 | 69.8 |
| 118770_soyisolate | 1.14 | 0.9 | 90.2 |
| AAE_AT_total6 | 35.43 | 5.1 | 16.7 |
| AAE_ATD_G_10.8.15 | 41.30 | 6.9 | 18.6 |
| AAE_ATD_G_10.8.15_II | 46.49 | 7.8 | 18.6 |
| AAE_BS_total2 | 14.56 | 3.1 | 26.1 |
| AAE_GA_total7 | 38.15 | 6.3 | 18.6 |
| AAE_KTD_16T_M1_20.8.15 | 32.18 | 6.2 | 21.8 |
| AAE_KTD_16T_M2_20.8.15 | 35.22 | 6.0 | 19.2 |
| AAE_P100_M1_16.2.15 | 24.95 | 2.5 | 13.3 |
| LED_ATD_G_10.8.15 | 40.11 | 7.4 | 20.4 |
| LED_ATD_G_10.8.15_II | 50.49 | 9.5 | 20.4 |
| LED_GA_16.4.15 | 29.08 | 3.9 | 16.3 |
| LED_GA_16.4.15_II | 28.98 | 3.9 | 16.3 |
| LED_KTD_6T_M1_20.8.15 | 20.75 | 4.9 | 27.2 |
| LED_KTD_M1_8.15 | 25.83 | 6.2 | 27.0 |
| LED_P100_16T_M2_30.3.15 | 12.94 | 2.4 | 24.0 |
| LSU_AT_total4 | 40.84 | 5.5 | 15.5 |
| LSU_KTD_16T_M1_20.8.15 | 90.30 | 7.3 | 9.1 |
| LSU_KTD_16T_M2_20.8.15 | 102.44 | 8.1 | 8.8 |
| PSA_Aro_G_18.8.15 | 37.46 | 3.5 | 11.6 |
| PSA_Aro_G_18.8.15_II | 35.75 | 3.3 | 11.6 |
| PSA_AT_total1 | 23.18 | 3.8 | 10.0 |
| PSA_AT_M1_G_5.8.15 | 37.46 | 7.0 | 20.7 |
| PSA_BS1_total 9 | 22.61 | 5.6 | 28.0 |
| PSA_BS2_31.3.15 | 13.57 | 3.1 | 28.0 |
| PSA_GA_total3 | 36.00 | 3.1 | 11.1 |
| PSA_KT_G_5.8.15 | 32.70 | 7.5 | 25.1 |
| PSA_KT_G_5.8.15_II | 34.17 | 7.8 | 25.1 |
| PSA_KTD_16T_M2_20.8.15 | 18.91 | 5.4 | 32.1 |
| PSA_KTD_3T_M2b_29.9.15 | 27.97 | 5.8 | 23.5 |
| PSA_KTD_4T_M2_14.9.15 | 14.97 | 3.9 | 30.7 |
| PSA_KTD_6T_M2a_14.9.15 | 20.94 | 3.8 | 21.9 |
| PSA_KTD_6T_M3_14-9.15 | 20.36 | 3.3 | 20.2 |
| PSA_KTD_6T_M3a_21.9.15 | 23.90 | 3.6 | 18.5 |
| PSA_KTD_9T_M3b_21.9.15 | 33.44 | 3.3 | 12.4 |
| PSA_P100_M1M2_21.8.15 | 20.17 | 3.3 | 20.1 |
| PSA_PM_M2 | 19.03 | 3.8 | 23.8 |
| PSA_ZT_20.2.15 | 54.84 | 5.1 | 10.9 |
| PSA_ZT_24.11.14 | 21.38 | 5.4 | 28.4 |
| SRU_BS_total5 | 17.95 | 5.4 | 34.0 |
| SRU_GA_total8 | 86.80 | 5.2 | 7.0 |
| WCO_Aro_G_18.8.15 | 32.93 | 3.4 | 12.9 |
| WCO_Aro_G_18.8.15_II | 30.77 | 3.1 | 12.9 |
| WCO_KTD_24T_M1_20.8.15 | 49.59 | 5.7 | 13.2 |
| WCO_ZT_24.11.14 | 32.42 | 3.7 | 14.0 |

Determination of the Biological Value:

Determination of the biological value for *Pleurotus sapidus*, cultivated on isomaltulose molasses, results in 73. Compared to other food, this value is surprisingly high (cf. Tab. 13).

TABLE 13

Comparison of the of the biological value for different food.

| Protein | Biological value |
|---|---|
| Egg | 100 |
| Pork | 85 |
| Beef | 80 |
| Poultry | 80 |
| Cow milk | 72 |
| Soy protein | 81 |
| Rye flour (82% milling) | 78 |
| Potatoes | 76 |
| Beans | 72 |

TABLE 13-continued

Comparison of the of the biological value for different food.

| Protein | Biological value |
|---|---|
| Rice | 66 |
| Wheat flour (82% milling) | 47 |

Example 11

Preparation and Recipe for a Vegan Bratwurst

Browning and browning taste are formed in conjunction with reducing sugars and mycelium of Basidiomycota, obtained from submerged culture, with various carbohydrate-rich agricultural tributaries. For this purpose, 13 different bratwursts were prepared as fine (I to IV) or coarse (VII to XIII) or a fine commercial "meaty" bratwurst (VII) variant with the following designations:
- I: without protein
- II: pea protein isolate
- III: sunflower protein concentrate
- IV: soy protein isolate
- V: soy protein concentrate
- VI: *Pleurotus sapidus* cultivated on isomaltulose molasses (PSA PM)
- VII: normal bratwurst (meat protein)
- VIII: without protein
- IX: pea protein isolate
- X: sunflower protein concentrate
- XI: soy protein isolate
- XII: soy protein concentrate
- XIII: *Pleurotus sapidus* cultivated on isomaltulose molasses (PSA PM)

The fine variation of the vegan bratwurst (I to VI) was prepared from 2 emulsions:
  a) Emulsion 1: 500 g emulsion 1 consisting of 0.85 g methylcellulose and 0.15 g corn flour with 13.3 g rape seed oil and 347 g ice water. The emulsion was prepared in the Thermomix (Year of manufacture 2010; TM31) on level 4 for 5 min.
  b) Emulsion 2: 500 g emulsion 2 consisting of 370 g ice water, 85 g rape seed oil, 4 g table salt, 1 g potassium chloride, 5 g citrus fiber, 20 g kappa-carrageen and 15 g pea starch instant. The emulsion was prepared in the Thermomix (see above) on level 6 for 5 min.

Subsequently both emulsions were combined and emulsified in the Thermomix on level 5 for 2 min.

Prior to the step of forming the emulsion, the following ingredients were added to 1,000 g emulsion consisting of 500 g emulsion 1 and 500 g emulsion 2:
5 g/kg Table salt
25 g/kg divers proteins or no additive:
- I: without protein
- II: pea protein isolate
- III: sunflower protein concentrate
- IV: soy protein isolate
- V: soy protein concentrate
- VI: *Pleurotus sapidus* on isomaltulose (PSA PM)

and 30 g/kg seasoning having the following recipe:

| | |
|---|---|
| Dextrose fine | 2.100 g |
| Table salt | 8.000 g |
| Pepper white milled | 2.500 g |
| Mace milled | 0.500 g |
| Ginger milled | 0.800 g |
| Macis base | 0.400 g |
| Citric acid E330 | 0.700 g |
| VM SMAK ® GOURMET WL | 6.000 g |
| Wurst flavor vegan | 4.000 g |
| Coarse broth w/o fe | 4.900 g |
| Lemon flavor (powder) | 0.100 g |

The emulsion and all mentioned ingredients were blended for further 2 min at level 6 in the Thermomix (as before).

The commercially available bratwurst (VII normal bratwurst) is prepared according to the following recipe:
200 g pork categorized according to GEHA SII
250 g pork leg meat
100 g pork cheeks
250 g pork bacon
200 g ice The following spices and additives were added to 1,000 g meat emulsion consisting of the above raw materials (in a total amount of 16 g/kg):

| | |
|---|---|
| Dextrose fine | 1.254 g |
| Table salt | 1.95 g |
| Phosphate E 450 | 1.05 g |
| Emulsifier E471 | 0.675 g |
| Emulsifier E472b | 0.075 g |
| Sodium carbonate E500 | 0.6 g |
| Glucose syrup | 1.15 g |
| Citrate E331 | 1.75 g |
| Pepper black base | 2.8 g |
| Silicic acid | 0.008 g |
| Macis Oleoresin liq | 0.064 g |
| Ginger Oleoresin liq | 0.024 g |
| Nutmeg base | 0.16 g |
| Cardamom milled | 0.28 g |
| Ginger de-oiled ground | 2.96 g |
| Seasoning | 1.2 g |

The bratwurst is prepared in the cutter of the company Seydelmann (series K60) as follows:

The meat is minced to the size of 3 mm using a MADO mincer (MEW613) and cut for 10 rounds with all ingredients at 3600 rpm. Then ⅓ of the ice is added and chopped for another 30 rounds at 3600 rpm. The lid of the cutter is cleaned from the inside, the remaining ice is added, and cutting is finished at 3600 rpm until the final temperature of 10° C. is reached.

The coarse variation of the vegan bratwurst (VIII to XIII) was prepared from 2 emulsions and wheat texturate with a proportional water content:
  a) Emulsion 1: 500 g emulsion 1 consisting of 0.85 g methylcellulose and 0.15 g corn flour with 133 g rape seed oil and 347 g ice water. The emulsion was prepared in the Thermomix on level 4 for 5 min.
  b) Emulsion 2: 500 g emulsion 2 consisting of 370 g ice water, 85 g rape seed oil, 4 g table salt, 1 g potassium chloride, 5 g citrus fiber, 20 g kappa-carrageen and 15 g pea starch instant. The emulsion was prepared in the Thermomix on level 6 for 5 min.

Subsequently both emulsions are combined.

900 g emulsion consisting of 450 g emulsion 1 and 450 g emulsion 2 and 100 g watered wheat texturate (33.35 g wheat texture dry and 66.65 g distilled water) were emulsified in the Thermomix at level 5 for 2 min.

The following ingredients were added before the emulsion formation step.

5 g/kg table salt
25 g/kg diverse proteins or no additive:
VIII: without protein
IX: pea protein isolate
X: sunflower protein concentrate
XI: soy protein isolate
XII: soy protein concentrate
XIII: PSA PM
And 30 g/kg seasoning according to the following recipe:

| | |
|---|---|
| Dextrose fine | 2.1 g |
| Table salt | 8.0 g |
| Pepper white milled | 2.5 g |
| Mace milled | 0.5 g |
| Ginger milled | 0.8 g |
| Macis base | 0.4 g |
| Citric acid E330 | 0.7 g |
| VM SMAK ® Gourmet WL | 6.0 g |
| Wurst flavor vegan | 4.0 g |
| Coarse broth w/o fe | 4.9 g |
| Lemon flavor | 0.1 g |

Figure 17:
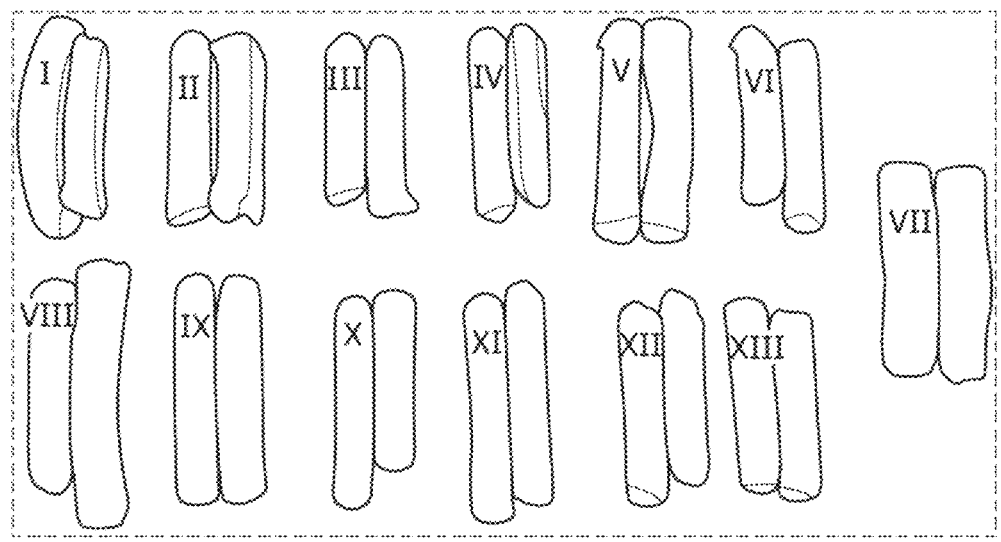
FIG. 17 shows an optical comparison of vegetarian "bratwursts" fine (I to VI) and commercial bratwurst on meat basis (VII) and vegetarian "bratwursts" coarse (VIII to XIII).
Figure 18:
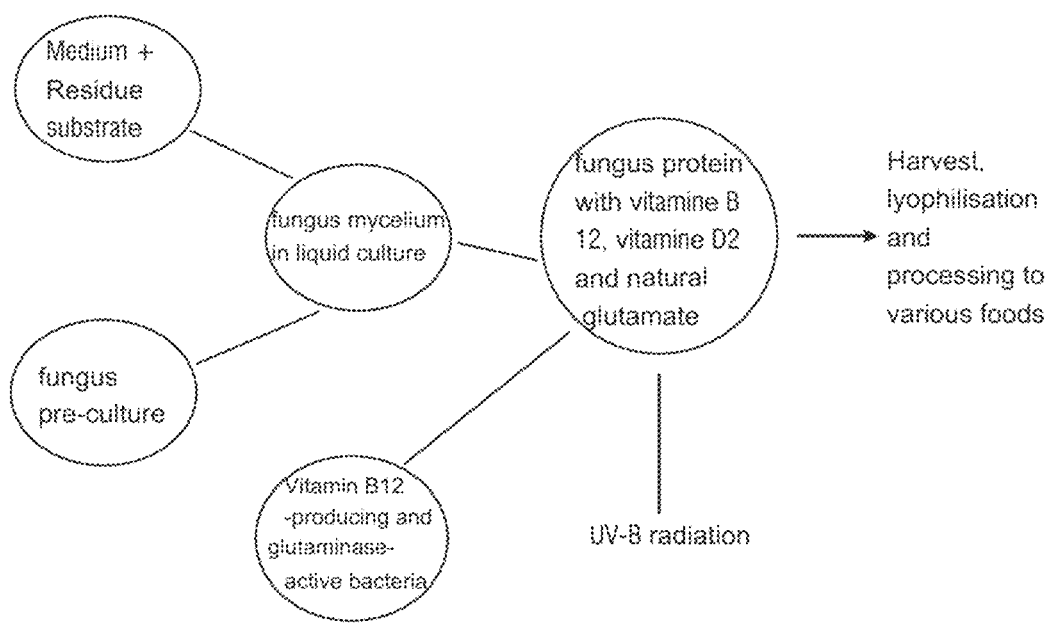
FIG. 18 shows a method according to the present invention for obtaining a product rich in proteins, vitamin B12 and vitamin D as well as containing glutamate.
Figure 19:
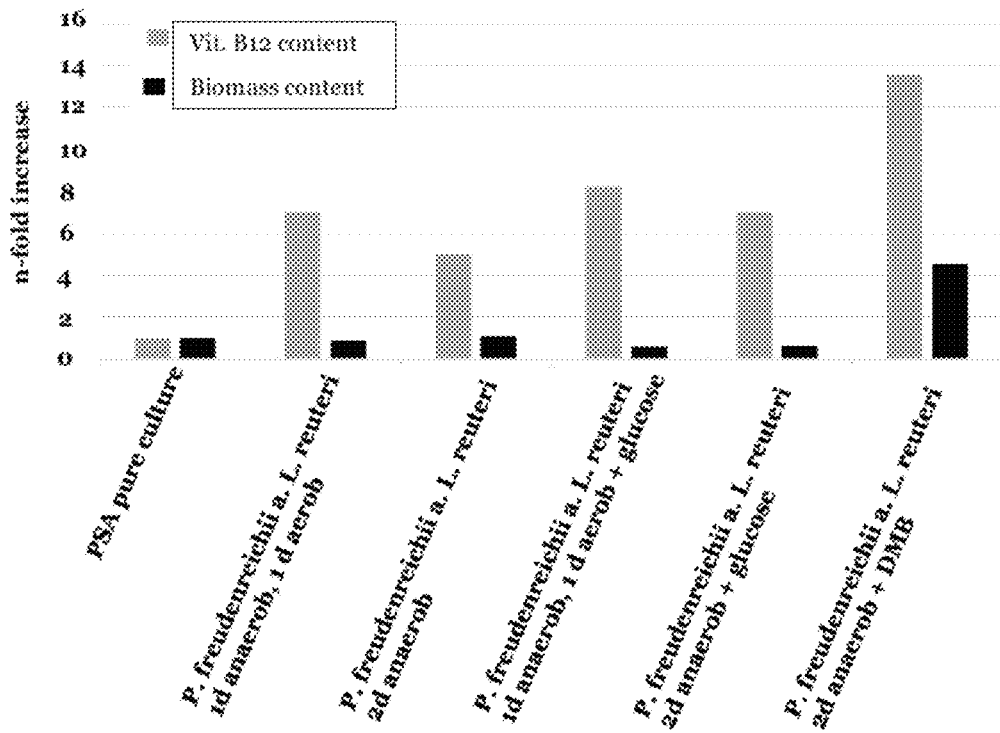
FIG. 19 shows the n-fold increase in biomass and vitamin B12 content of cultures consisting of *Pleurotus sapidus* (PSA) as well as cultures consisting of PSA, *P. freudenreichii* and *L. reuteri* under different cultivation conditions.

After thermal treatment for one hour at 85° C., the various bratwursts (FIG. 17) are cooled for 12 hours at 2° C. After a further 24 h, the bratwursts were tempered at room temperature for 3 h and subsequently thermally treated at 175° C. in the deep fryer for 3 min.

Compared to plant proteins, the protein-rich Basidiomycota mycelium (PSA on isomaltulose molasses) achieved the best results when browning in bratwurst. A significantly browner color after frying increases consumer acceptance, as most other plant proteins do not show this browning.

TABLE 14

Figure 14:
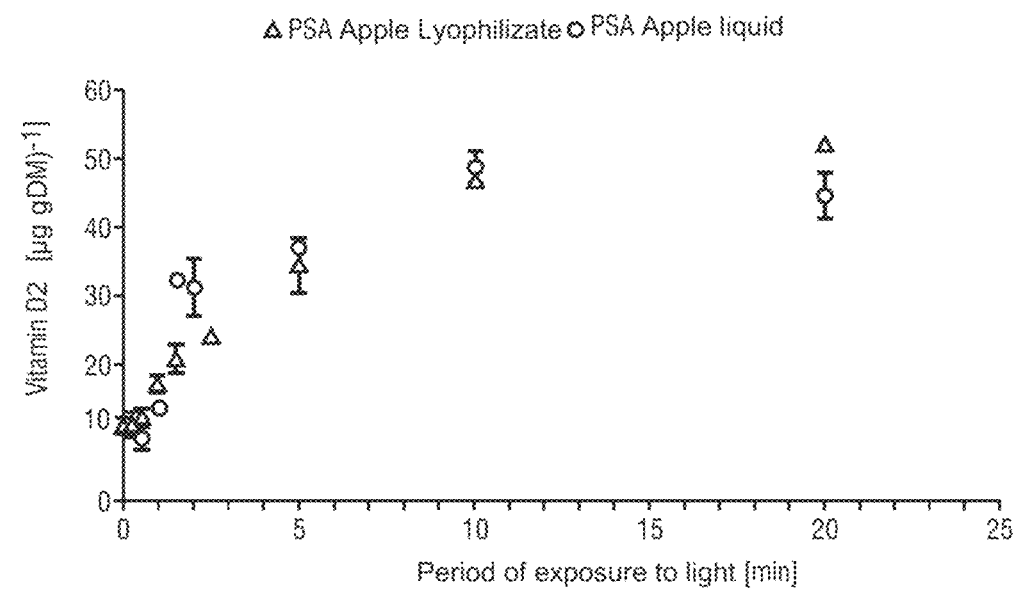
FIG. 14 shows the total RNA content in percent of an untreated and heated *Pleurotus sapidus* (PSA) culture on isomaltulose molasses.
Figure 15:
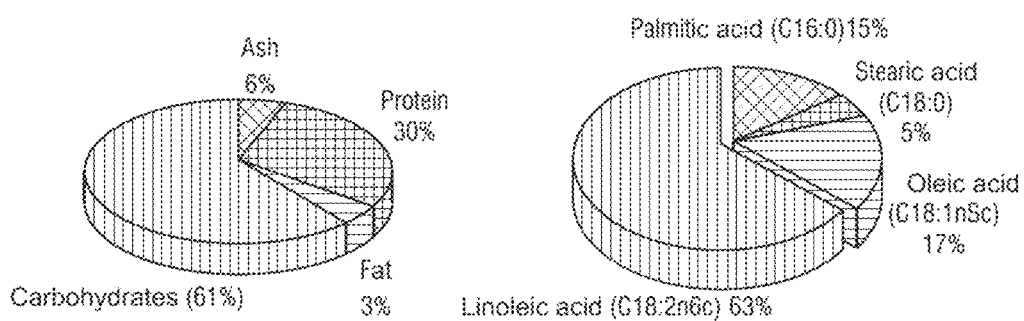
FIG. 15 shows the composition of *Pleurotus sapidus* (PSA) on isomaltulose molasses.

Visual classification of the various bratwursts with different proteins referring to FIG. 14.
Classification of the browning

| | Without addition of protein | Pea protein isolate | Sunflower protein concentrate | Soy protein isolate | Soy protein concentrate | Basidiomycota mycelium | Bratwurst/ meat |
|---|---|---|---|---|---|---|---|
| Without wheat texturate | (−) | (+) | (+) | (o) | (o) | (++) | |
| With wheat texturate | (−) | (+++) | (++) | (o) | (o) | (+++) | (++) |

(−) = bad frying performance
(+) = moderately good frying performance
(++) = optimum good frying performance according to consumer expectation
(+++) = excellent frying performance, time may be shortened
(o) = average frying performance

TABLE 15

Lxaxb-measurement of the bratwurst after
3 min at 175° C. in the deep fryer.

| | L | [SD] | a | [SD] | B | [SD] |
|---|---|---|---|---|---|---|
| Without wheat texturate | | | | | | |
| Without protein | 88.31 | ±0.11 | 0.35 | ±0.03 | 2.78 | ±0.08 |
| Pea protein isolate | 87.55 | ±0.12 | 0.30 | ±0.05 | 3.04 | ±0.09 |
| Sunflower protein conc. | 87.41 | ±0.21 | 0.23 | ±0.10 | 3.06 | ±0.10 |
| Soy protein isolate | 87.50 | ±0.14 | 0.14 | ±0.02 | 2.80 | ±0.07 |
| Soy protein conc. | 87.54 | ±0.06 | 0.18 | ±0.05 | 3.18 | ±0.10 |
| PSA_PM_15.07.2015 | 85.76 | ±0.11 | 0.45 | ±0.04 | 1.55 | ±0.12 |
| Normal bratwurst | 87.31 | ±0.02 | 0.20 | ±0.05 | 2.99 | ±0.03 |

TABLE 15-continued

Lxaxb-measurement of the bratwurst after
3 min at 175° C. in the deep fryer.

| | L | [SD] | a | [SD] | B | [SD] |
|---|---|---|---|---|---|---|
| With wheat texturate | | | | | | |
| Without protein | 86.35 | ±0.11 | 0.15 | ±0.05 | 1.79 | ±0.10 |
| Pea protein isolate | 85.76 | ±0.14 | 0.45 | ±0.04 | 1.55 | ±0.14 |
| Sunflower protein conc. | 86.03 | ±0.17 | 0.42 | ±0.08 | 2.14 | ±0.31 |
| Soy protein isolate | 86.42 | ±0.10 | 0.27 | ±0.04 | 2.12 | ±0.24 |
| Soy protein conc. | 86.49 | ±0.24 | 0.22 | ±0.06 | 2.08 | ±0.26 |
| PSA_PM_15.07.2015 | 85.73 | ±0.12 | 0.35 | ±0.04 | 1.57 | ±0.07 |

Example 12

Co-Cultivation of *Pleurotus sapidus, P. freudenreichii* and *L. reuteri*

Vitamin B12-producing *L. reuteri* or *P. freudenreichii* bacteria were added to a *Pleurotus sapidus* (PSA) pre-culture and further incubated aerobically or anaerobically for 24 h and 48 h, respectively, as described in Example 2. Glucose was additionally added in two of the cultures and 5,6-dimethylbenzimidazole (DMB), component of the vitamin B12 complex, was added in one of the cultures. The cultures were harvested after incubation and the increase in biomass and vitamin B12 content, respectively, was determined as described above. Specifically, by adding DMB the total biomass as well as the vitamin B12 content could be increased significantly.

Example 13

Co-Cultivation Using a Vegetarian Residue Substrate

A fungus/bacteria co-cultivation according to the present invention was carried out as described above in Example 2 and the increase in total biomass and bacterial content (in CFU/ml) were determined. For this purpose, minimal medium mixed with Palatinose, as described above, on the one hand, and minimal medium mixed with the food tributary whey, on the other hand, was used.

Both the biomass and the bacterial content could be increased by using whey as residual substrate compared to cultivations on Palatinose.

Example 14

Reactors for Co-Cultivation

Figure 20:
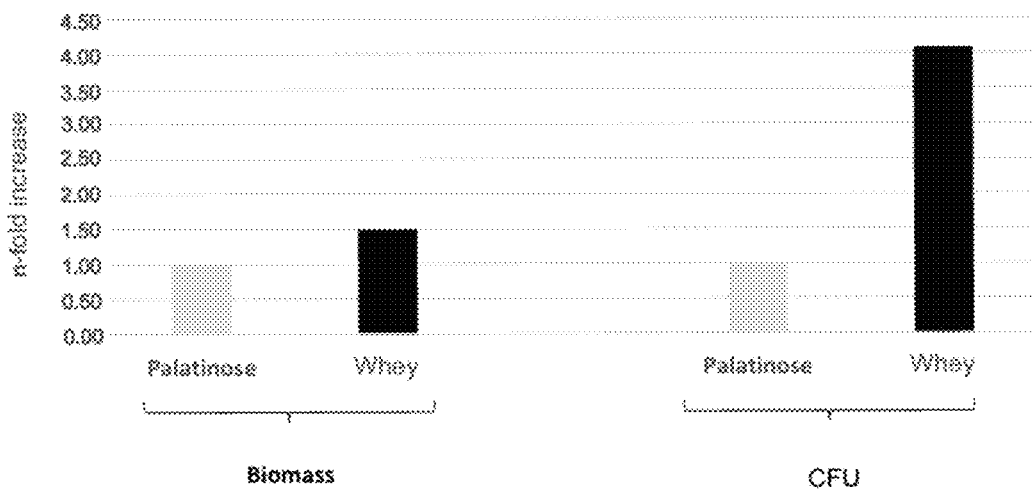
FIG. 20 shows the n-fold increase in biomass and bacteria content (in CFU/ml) when using Palatinose and whey, respectively.
Figure 21:
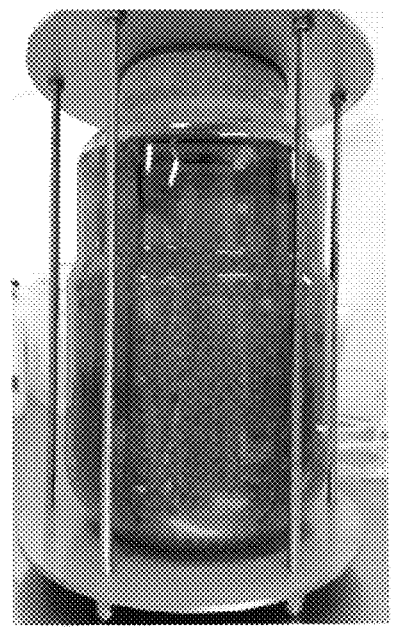
FIG. 21 shows a test reactor after 62 h cultivation of a PSA pure culture.
Figure 22:
FIG. 22 shows a test reactor during cultivation of a PSA pure culture.

A *Pleurotus sapidus* (PSA) pure culture was cultivated in 4 L experimental reactors. Two exemplary designs of the experimental reactors are shown in FIGS. 20 and 21. High PSA biomasses could be achieved by cultivation in the experimental reactors, for example during 62 h, as shown in FIG. 20.

The invention claimed is:

1. A method for producing a vitamin- and protein-rich product, comprising the steps:
   a) Cultivating in a vessel, at least one species of the division of Basidiomycota submerged in a nutrient medium comprising at least one carbohydrate-containing agricultural waste or food waste to obtain a first cultivation product;
   b) Adding at least one vitamin B12-producing species of the genus *Propionibacterium* and/or of the genus *Lactobacillus* to the first cultivation product, wherein the at least one vitamin B12-producing species is selected from the group consisting of *Propionibacterium freudenreichii* sups. *freudenreichii*, *Propionibacterium freudenreichii* sups. *shermanii*, *Lactobacillus reuteri*, and combination thereof; and
   c) Cultivating the at least one species of the genus *Propionibacterium* and/or at least one species of the genus *Lactobacillus* in the first cultivation product to obtain a second cultivation product,
   wherein the at least one species of the division of Basidiomycota is selected from the group consisting of *Agrocybe aegerita*, *Pleurotus roseus*, *Lentinula edodes*, *Laetiporus sulphureus*, *Pleurotus sapidus*, *Stropharia rugosoannulata*, *Wolfiporia cocos*, and mixtures thereof;
   wherein the second cultivation product is the vitamin- and protein-rich product.

2. The method according to claim 1, wherein the first cultivation product has a total biomass in the range of 5 to 45 g/L based on dry mass.

3. The method according to claim 1, wherein the second cultivation product has a total biomass in the range of 10 to 50 g/L based on dry mass.

4. The method according to claim 1, wherein the at least one carbohydrate-containing agricultural waste or food waste is selected from the group consisting of apple pomace, aronia pomace, spinach pomace, pomegranate pomace, beet molasses, isomaltulose molasses, sunflower seed pomace, onion pomace, draff, grape mare, hay and whey.

5. The method according to claim 1, wherein the nutrient medium used in step a) has 5 to 25 g/L carbohydrates.

6. The method according to claim 1, wherein the nutrient medium used in step a) further comprises:
   at least one nitrogen source, wherein the nitrogen source is selected from the group consisting of L-asparagine, ammonium nitrate and yeast extract;
   at least one magnesium source;
   at least one potassium source and/or phosphate source; and
   trace elements, wherein the trace elements comprise iron (II), zinc(II), copper(II) and manganese(II) compounds.

7. The method according to claim 1, wherein in step b) the at least one vitamin B12-producing species of the genus *Propionibacterium* and/or of the genus *Lactobacillus* is added such that a total viable count of all added bacteria species is in the range of $10^4$ to $10^{10}$ CFU/ml in the first cultivation product.

8. The method according to claim 1, wherein the step c) of cultivating the at least one species of the genus *Propionibacterium* and/or the at least one species of the genus *Lactobacillus* is performed until reaching a vitamin B12-concentration in the range of 1 to 20 ng/mL culture.

9. The method according to claim 1, wherein the method further comprises the steps of:
   d) Harvesting the at least one species of the division of Basidiomycota and the at least one vitamin B12-producing species of the genus *Propionibacterium* and/or *Lactobacillus* from the second cultivation product;
   e) Drying the harvested at least one species of the division of Basidiomycota and the at least one vitamin B12-producing species of the genus *Propionibacterium* and/or *Lactobacillus* to obtain dried vitamin- and protein-rich product.

10. The method according to claim 1, wherein the method further comprises the step of:
    irradiating the at least one species of the division of Basidiomycota at least partially with a UV-light source, wherein the step of irradiating may be performed during the whole process.

11. The method according to claim 1, wherein in step b) at least one glutaminase-active bacteria species from the genus *Lactobacillus* is further added.

12. The method according to claim 1, wherein the method is performed without harvesting the at least one species of the division of Basidiomycota from the first cultivation product.

13. The method of claim 1, wherein the vitamin- and protein-rich product is a food product.

14. The method of claim 13, wherein the food product is edible mushrooms.

* * * * *